US011911298B2

(12) United States Patent
Maitland et al.

(10) Patent No.: US 11,911,298 B2
(45) Date of Patent: *Feb. 27, 2024

(54) ROBUST ADAPTABLE FOOT PROSTHESIS

(71) Applicants: University of Washington, Seattle, WA (US); The Ohio Willow Wood Company, Mt. Sterling, OH (US)

(72) Inventors: Murray E. Maitland, Seattle, WA (US); Matthew M. Wernke, Seattle, WA (US); Evandro M. Ficanha, Seattle, WA (US); James M. Colvin, Seattle, WA (US)

(73) Assignees: University of Washington, Seattle, WA (US); The Ohio Willow Wood Company, Mt. Sterling, OH (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/347,785

(22) Filed: Jun. 15, 2021

(65) Prior Publication Data

US 2021/0307939 A1  Oct. 7, 2021

Related U.S. Application Data

(63) Continuation of application No. 15/925,574, filed on Mar. 19, 2018, now Pat. No. 11,076,970, which is a
(Continued)

(51) Int. Cl.
*A61F 2/66* (2006.01)
*A61F 2/50* (2006.01)

(52) U.S. Cl.
CPC .............. *A61F 2/6607* (2013.01); *A61F 2/66* (2013.01); *A61F 2002/5003* (2013.01);
(Continued)

(58) Field of Classification Search
CPC ..................................................... A61F 2/6607
See application file for complete search history.

(56) References Cited

U.S. PATENT DOCUMENTS 3,538,516 A * 11/1970 Gregory ................... A61F 2/60
623/48
3,889,300 A    6/1975 Smith
(Continued)

FOREIGN PATENT DOCUMENTS

DE   102005051646 A1 *  5/2007  ............... A61F 2/76
GB        1208421 A  * 10/1966
(Continued)

OTHER PUBLICATIONS

Basu et al., "Mobility one year after unilateral lower limb amputation; a modern, UK Institutional report, Interactive CardioVascular Throacic Surgery," 2008; 7:1024-1027.
(Continued)

*Primary Examiner* — Jacqueline Woznicki
(74) *Attorney, Agent, or Firm* — McDonnell Boehnen Hulbert & Berghoff LLP

(57) ABSTRACT

A device is provided to allow adaptation of a prosthetic or robotic foot in the medial-lateral direction, including pronation and supination of the foot using a series of articulations. Articulations are permitted in the disclosed device due to linkage systems positioned at various locations of the prosthetic foot. In particular, the device includes multiple connected linkage systems each including upper and lower portions with an articulating contact surface designed for load carriage and stability. The point of contact between the contact surfaces of each linkage system comprises the position-dependent instantaneous center of rotation of the
(Continued)

upper portion with respect to the lower portion. The device also includes a platform coupled between the linkage systems and a base.

20 Claims, 22 Drawing Sheets

Related U.S. Application Data continuation-in-part of application No. 15/154,515, filed on May 13, 2016, now Pat. No. 9,918,855.

(60) Provisional application No. 62/161,791, filed on May 14, 2015.

(52) U.S. Cl.
CPC ............... *A61F 2002/5009* (2013.01); *A61F 2002/5018* (2013.01); *A61F 2002/5043* (2013.01); *A61F 2002/5072* (2013.01); *A61F 2002/6614* (2013.01); *A61F 2002/6621* (2013.01); *A61F 2002/6642* (2013.01); *A61F 2002/665* (2013.01); *A61F 2002/6664* (2013.01)

(56) References Cited

U.S. PATENT DOCUMENTS

| | | | |
|---|---|---|---|
| 3,987,500 | A | 10/1976 | Schlein |
| 4,069,518 | A | 1/1978 | Groth |
| 5,674,296 | A | 10/1997 | Bryan |
| 6,187,052 | B1 | 2/2001 | Molino |
| 7,011,687 | B2 | 3/2006 | Deffenbaugh |
| 8,118,873 | B2 | 2/2012 | Humphreys |
| 2003/0199981 | A1 | 10/2003 | Ferree |
| 2005/0015157 | A1* | 1/2005 | Doddroe ............... A61F 2/76 623/49 |
| 2005/0043800 | A1 | 2/2005 | Paul |
| 2007/0083267 | A1 | 4/2007 | Miz |
| 2007/0233255 | A1 | 10/2007 | Song |
| 2008/0109084 | A1 | 5/2008 | Maitland |
| 2009/0270992 | A1 | 10/2009 | Gerber |
| 2009/0276051 | A1 | 11/2009 | Arramon et al. |
| 2012/0078313 | A1 | 3/2012 | Hasse |
| 2012/0130508 | A1* | 5/2012 | Harris ............... A61F 2/68 623/50 |
| 2012/0203359 | A1* | 8/2012 | Schimmels ........... A61F 2/6607 623/55 |
| 2013/0123927 | A1 | 5/2013 | Malandain |
| 2013/0274880 | A1 | 10/2013 | Arramon |
| 2015/0230943 | A1* | 8/2015 | Marlin ............... A61F 2/68 623/47 |
| 2016/0367384 | A1* | 12/2016 | Sigmon ............... A61F 2/76 |

FOREIGN PATENT DOCUMENTS

| | | | | |
|---|---|---|---|---|
| WO | WO-2007048404 | A2 * | 5/2007 | ............... A61F 2/76 |
| WO | WO-2012077141 | A1 * | 6/2012 | ........... A61F 2/6607 |
| WO | WO-2014109723 | A1 * | 7/2014 | ........... A61F 2/6607 |

OTHER PUBLICATIONS

Bui et al., "Skin problems in individuals with lower limb loss: Literature review and proposed classification system," J. Rehab Res. Dev.; 2009; 46-1085-1090.

Gailey et al., "Review of secondary physical conditions associated with lower limb amputation and long term prosthesis use," J. Rehab. Res. Dev. 2008; 45:15-30.

Gold et al., "Anatomic and etiological classification of congenital limb deficiencies," Am. J. Med. Genet. Part A, 2011; 155:1225-1235.

Hall et al., "Cognitive and motor mechanisms underlying older adults' ability to divide attention while walking," Phys. Ther., 2011; 91:1039-1050.

Kruger et al., "Ten years at war: Comprehensive analysis of amputation trends," J. Trauma Acute Care Surg. 2012; 73:S438-S444.

Kulkarni et al., "Falls in patients with lower limb amputations: Prevalence and contributing factors," Physiother. 1996:130-136.

Meulenbelt et al., "Skin problems of the stump in lower limb amputees: 2. Influence on functioning in daily life," Acta Derm. Venereol 2011; 91:178-182.

Miller et al., "A prospective study examining balance confidence among individuals with lower limb amputation," Disability Rehab., 2004; 26:875-881.

Miller et al., "The influence of balance confidence on social activity after discharge from prosthetic rehabilitation for first lower limb amputation," Prosthet. Orthot. Int., 2011; 35:379-385.

Miller et al., "The prevalence and risk factors of falling and fear of falling among lower extremity amputees," Arch Phys. Med. Rehabil., 2001; 82:1031-1037.

Robbins et al., "A review of the long term health outcomes associated with war related amputation," Military Med., 2009; 174:588-592.

Wrobel et al., "Geographic variation of lower extremity major amputation in individuals with and without diabetes in the medicare population," Diabetes Care, 2001; 24:860-864.

* cited by examiner

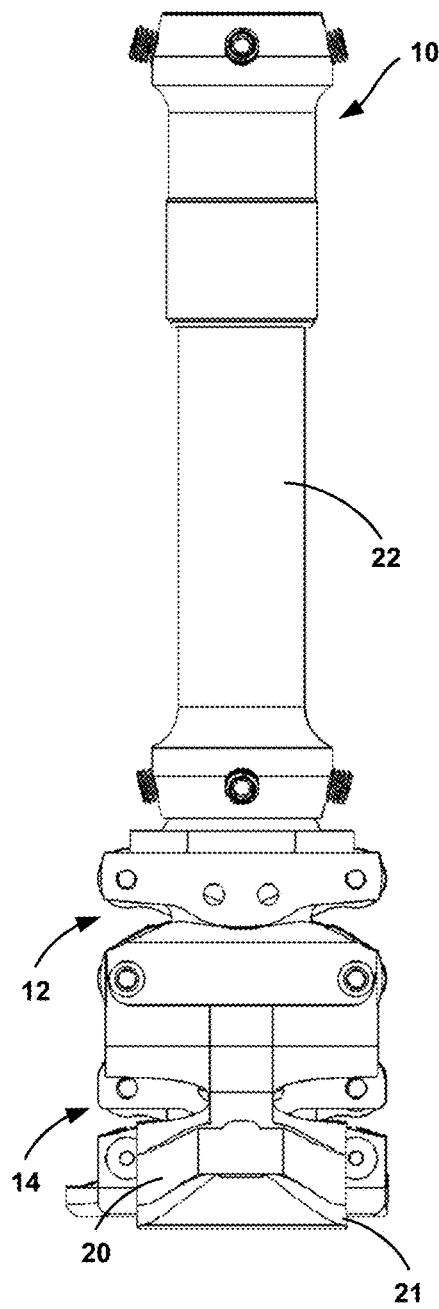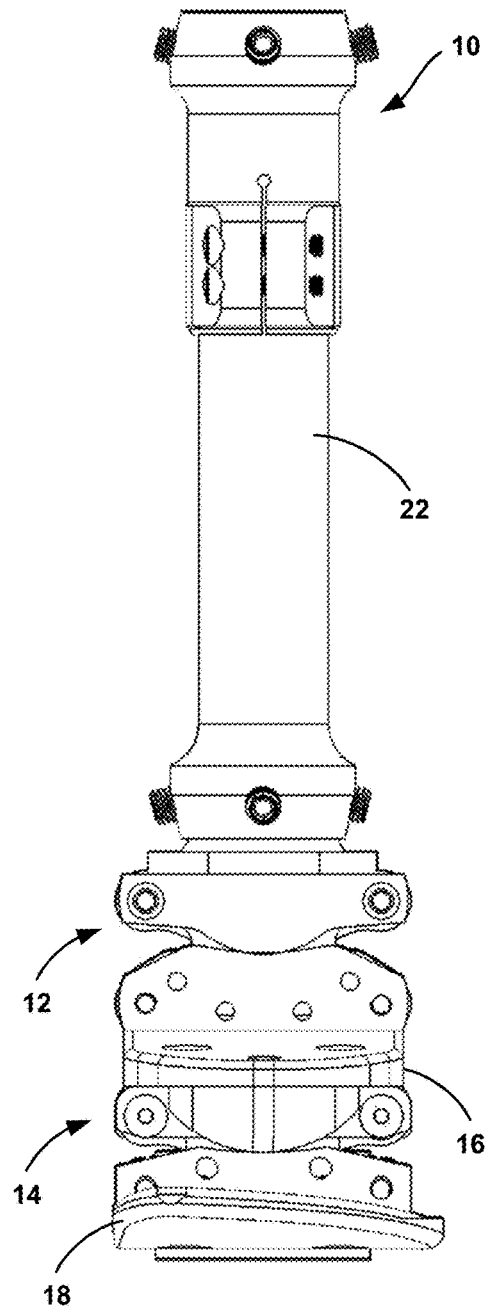
Fig. 8                    Fig. 9

ROBUST ADAPTABLE FOOT PROSTHESIS

CROSS-REFERENCE TO RELATED APPLICATIONS

This application is a continuation of U.S. Non-Provisional application Ser. No. 15/925,574, filed on Mar. 19, 2018, which is a continuation-in-part of U.S. patent application Ser. No. 15/154,515, filed May 13, 2016, which claims the benefit of U.S. Provisional Patent Application Ser. No. 62/161,791, filed May 14, 2015, the entire contents of each of which are herein incorporated by reference.

STATEMENT REGARDING FEDERAL FUNDING

This invention was made with government support under Grant No. 5R42HD093476-03, awarded by the National Institutes of Health (NIH). The government has certain rights in the invention.

BACKGROUND

Unless otherwise indicated herein, the materials described in this section are not prior art to the claims in this application and are not admitted to be prior art by inclusion in this section.

In the normal ankle and foot there is an anatomical chain of movement from the ankle joint to the toes. In particular, a normal foot has a series of articulations with increasing levels of motion, including the talocrural (ankle) joint, the subtalar (heel) joint, the tarsal (midfoot) joint, and the metatarsals and phalanges (forefoot). The sequence of the articulations of a normal foot permits variations in lateral motions depending on the surface coming into contact with the foot, or the position of the body above the foot. When lower extremity amputations result due to abnormal development, trauma, diabetes, or some other medical condition, these amputations of the leg or ankle result in chronic disability. This is because conventional prosthetic foot designs do not sufficiently replace the anatomical function of the foot to accommodate sideways motions. As such, medio-lateral stresses remain a significant problem with current prosthetics, especially on slide-slopes, uneven ground, turning, or where there is uncertainty of placement of the foot such as during cognitive tasks while ambulating.

Pain and skin breakdown at the residual limb remains a problem in current prosthetics in part because of shear stresses induced by forces on the socket. Skin breakdown may cause limitations in many activities of daily living. Additionally, gait is an attention-demanding task, and any concurrent cognitive task, even a very simple one, may disrupt walking performance. The current mechanical designs of existing prostheses are believed to be related to back pain, residual limb pain, and contralateral knee pain along with early osteoarthritis. As a result, many aspects of an individual's physical performance are chronically affected with use of a prosthetic device, not only those associated with walking. If physical activity is reduced, chronic diseases such as cardiovascular disease or impaired glucose metabolism are at increased risk.

SUMMARY

Example devices described herein allow adaptation of a prosthetic foot in the medial-lateral direction, including pronation and supination of the prosthetic foot. The device described herein may mimic the functions of a normal foot using a series of articulations. Articulations are permitted in the disclosed devices due to linkage systems positioned at various locations of the prosthetic foot, as described in more detail below. The disclosed devices may improve walking, running, and other forms of bipedal motion (such as dancing) for people with prosthetic feet. In particular, the disclosed devices may allow for level placement of the leg over the foot on uneven ground or a medial-lateral grade during walking and running. The disclosed devices may further accommodate variations in leg position over the foot for a person with poor coordination. In addition, the disclosed devices may permit variations in leg position on a level surface for people participating in various recreational activities such as dance or racquet sports. Legged robotic devices may also benefit from the mechanical adaptations of the invention to make them more versatile and functional traversing variable terrain.

Thus, in one aspect, a device is provided including (a) a first linkage system and a second linkage system, each linkage system including (i) a first upper portion having a first contact surface, (ii) a first lower portion having a second contact surface, wherein the second contact surface contacts the first contact surface, (iii) a first tension bearing element with a first end pivotally coupled to a first end of the first lower portion and a second end pivotally coupled to a second end of the first upper portion, and (iv) a second tension bearing element with a first end pivotally coupled to a second end of the first lower portion and a second end pivotally coupled to a first end of the first upper portion, (b) a platform coupled to one of the first upper portion or the first lower portion of the first linkage system and further coupled to the first upper portion of the second linkage system, and (c) a base coupled to the first lower portion of the second linkage system.

In a second aspect, the device may further include (d) a third linkage system, including (i) a third upper portion having a third contact surface, (ii) a third lower portion having a fourth contact surface, wherein the fourth contact surface contacts the third contact surface, (iii) a third tension bearing element with a first end pivotally coupled to a first end of the third lower portion and a second end pivotally coupled to a second end of the third upper portion, and (iv) a fourth tension bearing element with a first end pivotally coupled to a second end of the third lower portion and a second end pivotally coupled to a first end of the third upper portion, wherein the first upper portion of the first linkage system is coupled to the platform and the third lower portion of the third linkage system is coupled to one of the platform or the first upper portion of the first linkage system, and wherein the plane of rotation of the third upper portion of the third linkage system is perpendicular to the plane of rotation of the first upper portion of the first and second linkage systems.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 8 is a rear view of the prosthetic device, according to the example embodiment of FIG. 1.

FIG. 9 is a front view of the prosthetic device, according to the example embodiment of FIG. 1.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means +/−5%.

Standing atop a typical artificial leg without medial-lateral accommodation to the ground surface is analogous to standing on stilts. The long lever-arm of the leg makes it such that the center of mass of the body falls outside of the base of support without much angle of the leg with respect to the base. Example devices described herein may allow adaptation of a prosthetic foot in the medial-lateral direction, including pronation and supination of the prosthetic foot. The devices described herein may mimic the functions of a normal foot using a series of articulations. The articulations may be permitted via linkage systems positioned at various locations of the prosthetic foot, as described in more detail with reference to the figures below.

Figure 1:
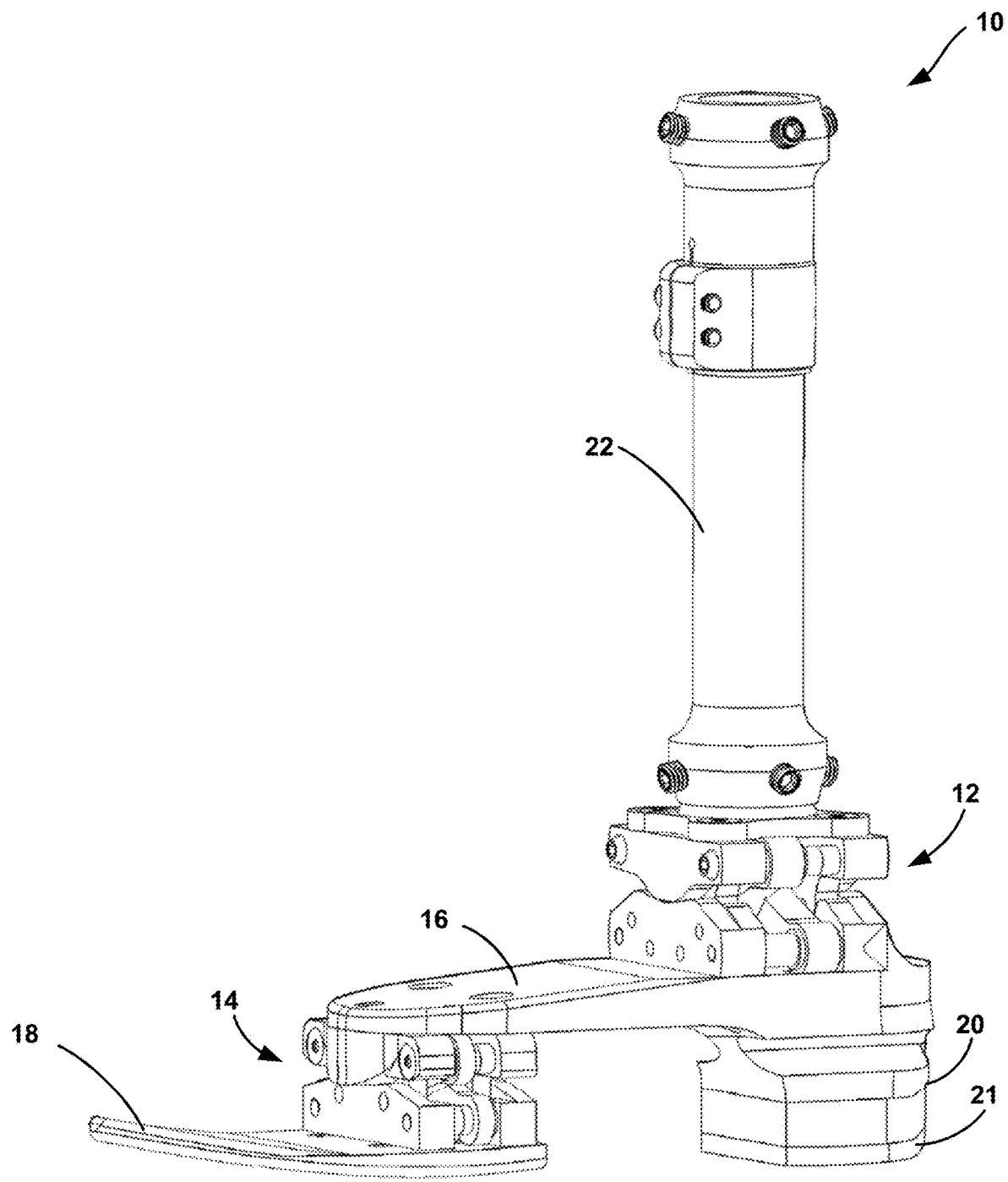
FIG. 1 is a perspective view of a prosthetic device, according to one example embodiment.

In a first aspect, FIG. 1 illustrates an example prosthetic device 10 in accordance with one embodiment of the invention. The prosthetic device 10 may include a first linkage system 12 and a second linkage system 14. The first linkage system 12 may be an ankle linkage component of the prosthetic device 10, and the second linkage system 14 may be a forefoot linkage component. The plane of rotation of the first linkage system 12 may be substantially parallel to the plane of rotation of the second linkage system 14. In other words, like components of the first linkage system 12 and the second linkage system 14 are facing the same direction, as shown in FIG. 1. The prosthetic device 10 may also include a platform 16 coupling the first linkage system 12 to the second linkage system 14. The prosthetic device 10 may further include a base 18 coupled to a lower portion of the second linkage system 14.

Figure 2:
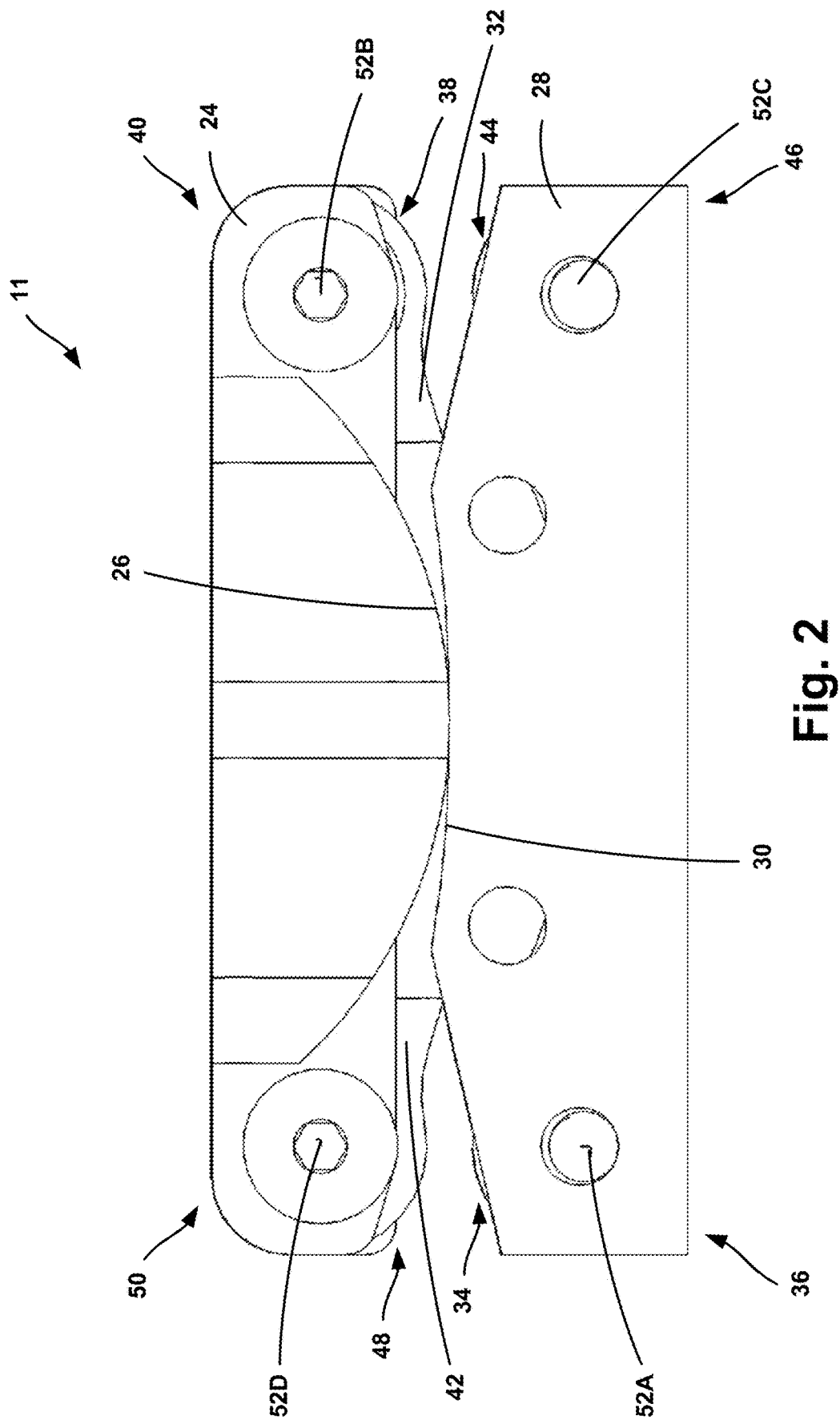
FIG. 2 is a side view of an example linkage system of the prosthetic device, according to an example embodiment.
Figure 3:
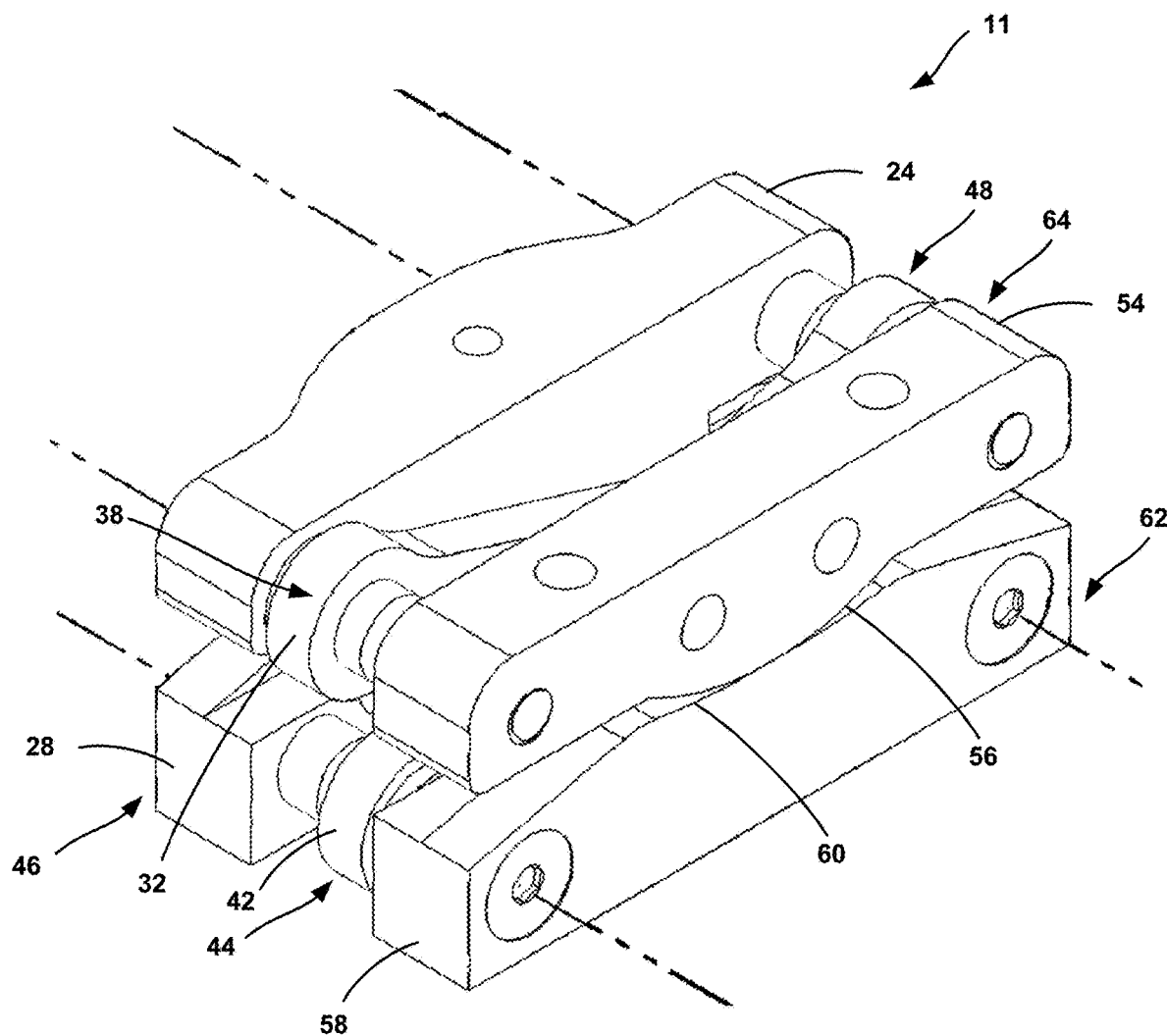
FIG. 3 is a perspective view of the example linkage system, according to the example embodiment of FIG. 2.
Figure 4:
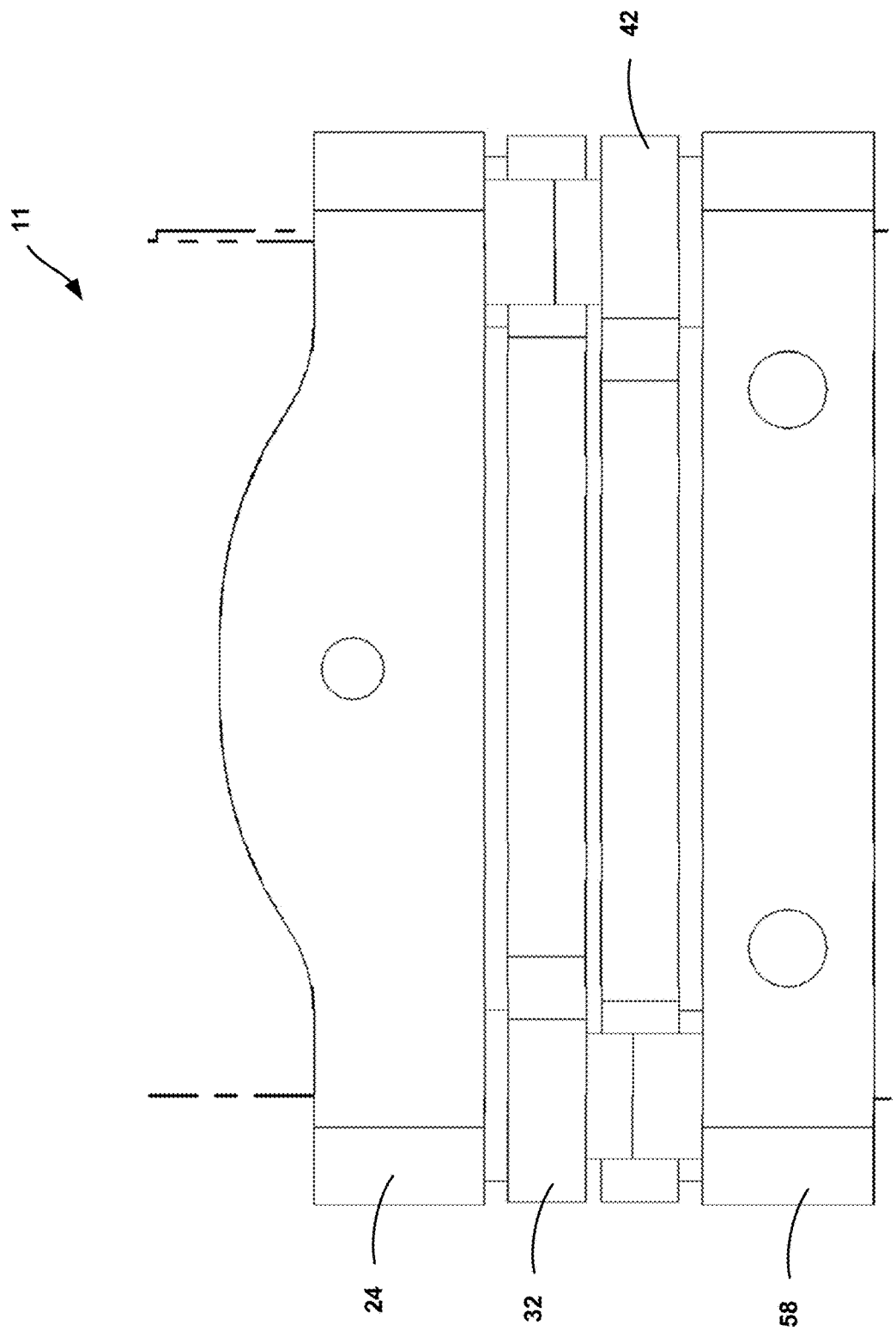
FIG. 4 is a top view of the example linkage system, according to the example embodiment of FIG. 2.

FIG. 2 illustrates a side view of an example linkage system 11 of the prosthetic device 10. FIG. 3 illustrates a perspective view of the linkage system 11 of FIG. 2, and FIG. 4 illustrates a top view of the linkage system 11 of FIG. 2. The first linkage system 12, the second linkage system 14, and other linkage systems described herein may be configured similarly to the linkage system 11 shown in FIGS. 2-6. In particular, as shown in FIG. 2, the linkage system 11 may include a first upper portion 24 having a first contact surface 26. The linkage system 11 may further include a first lower portion 28 having a second contact surface 30, where the second contact surface 30 contacts the first contact surface 26. In particular, as shown in FIG. 2, the first contact surface 26 of the linkage system 11 comprises a convex surface, and the second contact surface 30 of the linkage system 11 comprises a concave surface.

In one example, the first contact surface 26 comprises a first material, and the second contact surface 30 comprises a second material that is different than the first material. In one particular example, the first contact surface comprises aluminum, stainless steel, or titanium, while the second contact surface comprises polyoxymethylene, polyethylene, or nylon. Other examples are possible as well. In one example, the entire first upper portion 24 may comprise the materials described above for the first contact surface 26. In another example, the first upper portion 24 is coated with a different material at the first contact surface 26, such that the material at the first contact surface 26 is different than the material of the rest of the first upper portion 24. Similarly, in one example the entire first lower portion 28 may comprise the materials described above for the second contact surface 30. In another example, the first lower portion 28 is coated with a different material at the second contact surface 30, such that the material at the second contact surface 30 is different than the material of the rest of the first lower portion 28.

The linkage system 11 further includes a first tension bearing element 32 with a first end 34 pivotally coupled to a first end 36 of the first lower portion 28 and a second end 38 pivotally coupled to a second end 40 of the first upper portion 24. The linkage system 11 further includes a second tension bearing element 42 with a first end 44 pivotally coupled to a second end 46 of the first lower portion 28 and a second end 48 pivotally coupled to a first end 50 of the first upper portion 24. In one example, the first tension bearing element 32 and/or the second tension bearing element 42 may be a rigid bar or other rigid component capable of receiving tensile and compressive forces. In another example, the first tension bearing element 32 and/or the second tension bearing element 42 may be a cable or such component capable of receiving tensile forces, but not compressive forces.

The first end 34 of the first tension bearing element 32 may be pivotally coupled to the first end 36 of the of the first lower portion 28 via axle 52A, and the second end 38 of the first tension bearing element 32 may be pivotally coupled to the second end 40 of the first upper portion 24 via axle 52B. The axles 52A, 52B may be configured to pass through a corresponding hole in the first lower portion 28 and first upper portion 24, respectively, and corresponding holes in the first tension bearing element 32. Similarly, the first end 44 of the second tension bearing element 42 may be pivotally coupled to the second end 46 of the first lower portion 28 via axle 52C, and the second end 48 of the second tension bearing element 42 may be pivotally coupled to the first end 50 of the first upper portion 24 via axle 52D. The axles 52C, 52D may be configured to pass through a corresponding hole in the first lower portion 28 and first upper portion 24, respectively, and corresponding holes in the second tension bearing element 42.

In one example, the linkage system 11 may further include a third tension bearing element with a first end pivotally coupled to the first end 36 of the first lower portion 28 and a second end pivotally coupled to the second end 40 of the first upper portion 24, and a fourth tension bearing element with a first end pivotally coupled to a second end 46 of the first lower portion 28 and a second end pivotally coupled to a first end 50 of the first upper portion 24. In such an example, the linkage system 11 includes a pair of opposing tension bearing elements on each side of the first upper portion and first lower portion.

In another example, such as the example shown in FIG. 3, the linkage system may further include a second upper portion 54 having a third contact surface 56, and a second lower portion 58 having a fourth contact surface 60. The third contact surface 56 contacts the fourth contact surface 60. In particular, the third contact surface 56 of the linkage system 11 comprises a convex surface, and the fourth contact surface 60 of the linkage system 11 comprises a concave surface. Further, the first end 34 of the first tension bearing element 32 is pivotally coupled to a first end 62 of the second lower portion 58 and a second end 38 of the first tension bearing element 32 is pivotally coupled to the second end 40 of the first upper portion 24. Further, the first end 44 of the second tension bearing element 42 is pivotally coupled to the second end 46 of the first lower portion 28 and the second end 48 of the second tension bearing element 42 is pivotally coupled to the first end 64 of the second upper portion 54. Other arrangements are possible as well.

In one embodiment, the linkage system 11 includes at least one spring mechanism configured to return the linkage system 11 to a position of repose when the device is unweighted. In one example, the spring mechanism comprises a compliant material disposed between the first upper portion 24 and the first lower portion 28 and/or between the second upper portion 54 and the second lower portion 58. In another example, the spring mechanism comprises an actuator disposed between the first upper portion 24 and the first lower portion 28 and/or between the second upper portion 54 and the second lower portion 58. The at least one spring mechanism may be configured to transition the linkage system 11 from a weighted height to an unweighted height. For example, in operation a wearer of the prosthetic device 10 may step on an inclined surface at an angle to the incline, as discussed in more detail below in relation to FIGS. 5 and 6. In such a case, on one side of the linkage system 11, the first lower portion 28 moves closer to the first upper portion 24. At the same time on the opposite side of the linkage system 11, the first upper portion 24 moves further away from the first lower portion 28. As the wearer lifts the device 10 off of the inclined surface, the at least one spring mechanism may return or assist with returning the linkage system 11 to a position of repose before the wearer places the foot back on the ground. Further, the at least one spring mechanism may be used to modify rotational properties of the first lower portion 28 with respect to the first upper portion 24.

The length-to-height ratio of the linkage system 11 may vary. In one example, the length-to-height ratio may be greater than 1.5:1. For example, the length-to-height ratio of the linkage system may be 2:1, or 3:1. It may desirable to keep the center of rotation of the linkage system 11 relatively low, so as to keep the center of rotation within the base of support at the maximal angular position. The physical size of the linkage system 11 is scalable within the desired length-to-height ratio.

As discussed above, each of the first linkage system 12 and the second linkage system 14 described above, and the third linkage system described below may have each of the components of linkage system 11. However, the linkage systems may be slightly different from one another. For example, the second linkage system 14 may have a shorter length and shorter height than the length and height of the first linkage system 12. Such a configuration may be advantageous for fitting the prosthetic device 10 in a shoe or other housing, as examples. In another example, each of the linkage systems may have varying length to height ratios to match their desired function in the prosthetic device 10. As another example, each linkage system may have a defined maximum rotation to better mimic their corresponding joints of a human foot. The at least one spring mechanism may be used to define the maximum rotation for each linkage system. In another example, the structure of the linkages themselves may define the maximum angle of rotation. In one example, the maximum angle between the first upper portion 24 of the first linkage system 12 and the first lower portion 28 of the first linkage system 12 may be between about ten and twenty degrees. As another example, the maximum angle between the first upper portion 24 of the second linkage system 14 and the first lower portion 28 of the second linkage system 14 may be between about twenty and forty-five degrees.

As discussed above, the prosthetic device 10 may also include a platform 16 coupling the first linkage system 12 to the second linkage system 14. In particular, as shown in FIG. 1, the first lower portion 28 of the first linkage system 12 may be coupled to a top surface of the platform 16, and the first upper portion 24 of the second linkage 14 may be coupled to a bottom surface of the platform 16. The platform 16 may include carbon fiber, a carbon fiber composite, a high density nylon material, polyoxymethylene, or combinations thereof, amongst other possibilities. In one example, the platform 16 may be a flexible bridging platform coupling the first linkage system 12 to the second linkage system 14. In another example, the platform 16 may be a rigid brace, a bar, and/or a span coupling the first linkage system 12 to the second linkage system 14. In either case, the platform 16 may mimic a tarsal joint (midfoot) of a normal foot to supply a balance of rigidity and spring to the foot function.

As weight moves from hindfoot to forefoot, the platform 16 accommodates unevenness between the front and back ground level, as well as the angle of the user's leg relative to the floor. As the wearer of the prosthetic device 10 shifts their weight forward, the platform 16 may act as a springboard propelling the wearer forward in bipedal motion. In one example, the platform 16 may have a level bottom surface, such that the first upper portion 24 of the first linkage system 12 and the top surface of the hindfoot support 20 are substantially parallel. In another example, the platform 16 may have a two-tiered bottom surface. The two-tiered bottom surface of the platform 16 may cause the height of the second linkage system 14 to be less than the height of the hindfoot support 20. Such a configuration may be advantageous for fitting the prosthetic device 10 in a shoe, as an example. The preferred position of the two-tiered bottom surface of the platform 16 may be adjusted based on the particular user, and the particular footwear of the user. For example, higher heeled shoes will need more angulation of the two-tiered bottom surface. Other configurations are possible as well.

As discussed above, the prosthetic device 10 may further include a base 18 coupled to a lower portion of the second linkage system 14. The base 18 may include a forefoot pad coupled to the first lower portion 28 of the second linkage system 14 and a flexible toe pad extending from the first lower portion 28 of the second linkage system 14 in a direction away from the first linkage system 12. The base 18 may include carbon fiber, a carbon fiber composite, a high density nylon material, polyoxymethylene, or combinations thereof, among other possibilities. As shown in FIG. 1, the first linkage system 12 may be coupled to a hindfoot support 20. In particular, an upper surface of the hindfoot support 20 may be coupled to the platform 16, while a lower surface of the hindfoot support 20 may be coupled to a hindfoot pad 21. The hindfoot pad 21 may include a rounded end to ease bipedal motion and accommodate a user's heel strike against the ground surface.

In one example, a prosthetic limb 22, such as a shank, may be coupled to the platform 16, in a position above the first linkage system 12. A bottom portion of the prosthetic limb 22 may include a connector portion that is configured to mate with a connector portion positioned on the platform 16. In another embodiment, the device 10 may be coupled to a robotic device, such as a leg of a legged robotic device. Other connection mechanisms are possible as well.

The prosthetic device 10 may further include a housing sized and shaped to receive the prosthetic device 10. For example, the housing may be a shoe that encompasses the prosthetic device 10. In another example, the housing may be shaped like a human foot. Other examples are possible as well.

Figure 5:
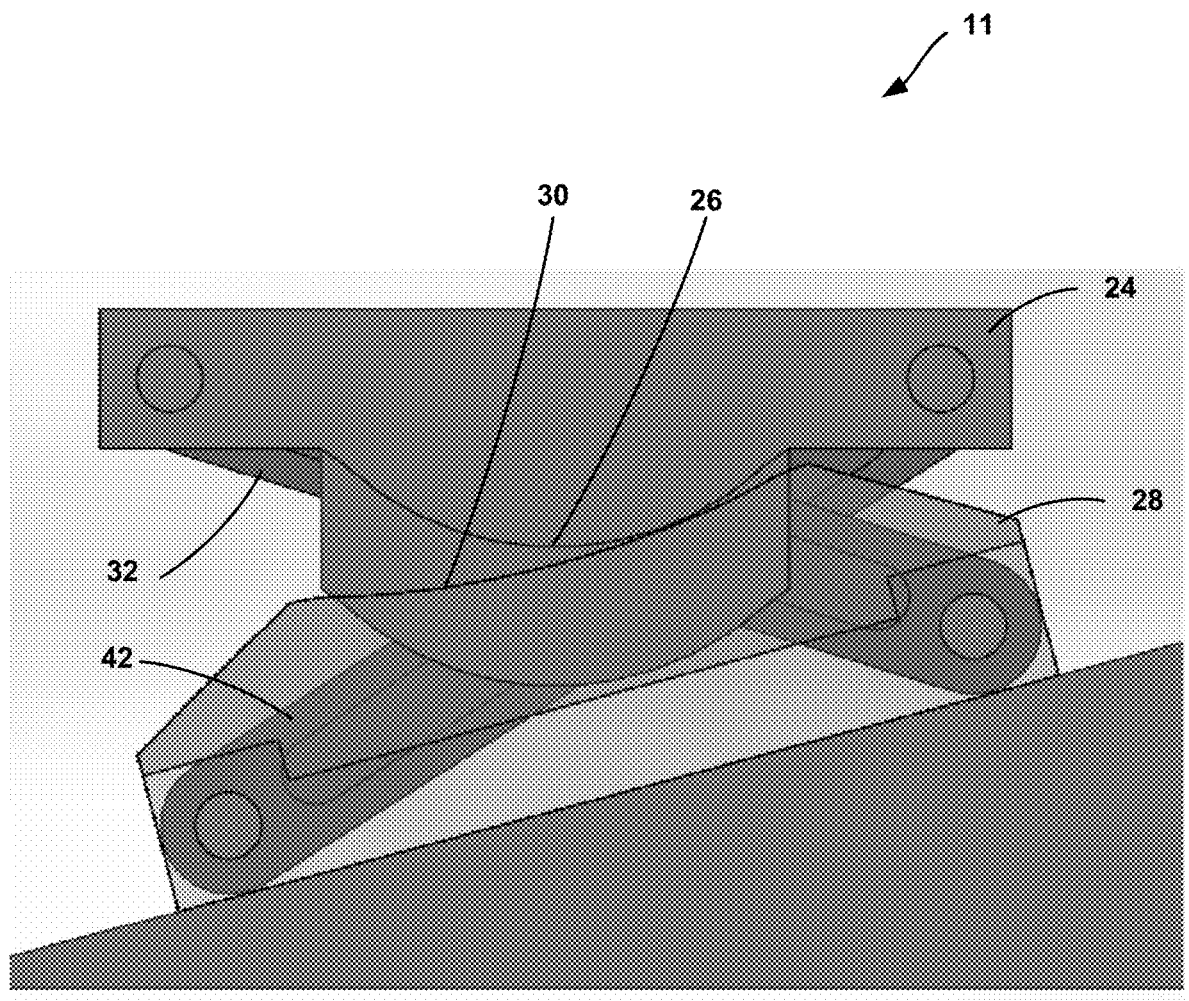
FIG. 5 shows the linkage system of FIG. 2 on an incline, according to the example embodiment of FIG. 2.

FIG. 5 illustrates the linkage system 11 on a medial-lateral grade, according to an example embodiment. As the base 18 and hindfoot pad 20 contacts uneven ground, the first lower portion 28 of the first linkage system 12 and of the second linkage system 14 rotate, and becomes parallel to the ground surface. At the same time, the first upper portion 24 of the first linkage system 12 and of the second linkage system 14 remain perpendicular to the prosthetic limb 22. As the first upper portion 24 rotates with respect to the first lower portion 28, the first contact surface 26 remains in contact with the second contact surface 60. In particular, the contact between the first contact surface 26 and the second contact surface 30 of each linkage system comprises an instantaneous center of rotation of the first upper portion 24 with respect to the first lower portion 28. The instantaneous center of rotation is the point fixed to a body undergoing planar movement that has zero velocity at a particular instant of time. At this instant, the velocity vectors of the trajectories of other points in the body generate a circular field around this point which is identical to what is generated by a pure rotation. As such, each linkage system described herein includes a weight-bearing surface that follows the instantaneous center of rotation of the linkage system. The surface geometry of the first contact surface 26 and/or the second contact surface 30 of each linkage system described herein may be determined by the instantaneous center of rotation of the linkage system. As such, the point of contact between the contact surfaces of each linkage system comprises the position-dependent instantaneous center of rotation of the first upper portion 24 with respect to the first lower portion 28. With such a configuration, side-to-side motion with balance and stability is maintained because the position of the center of rotation varies with the applied forces.

Figure 6:
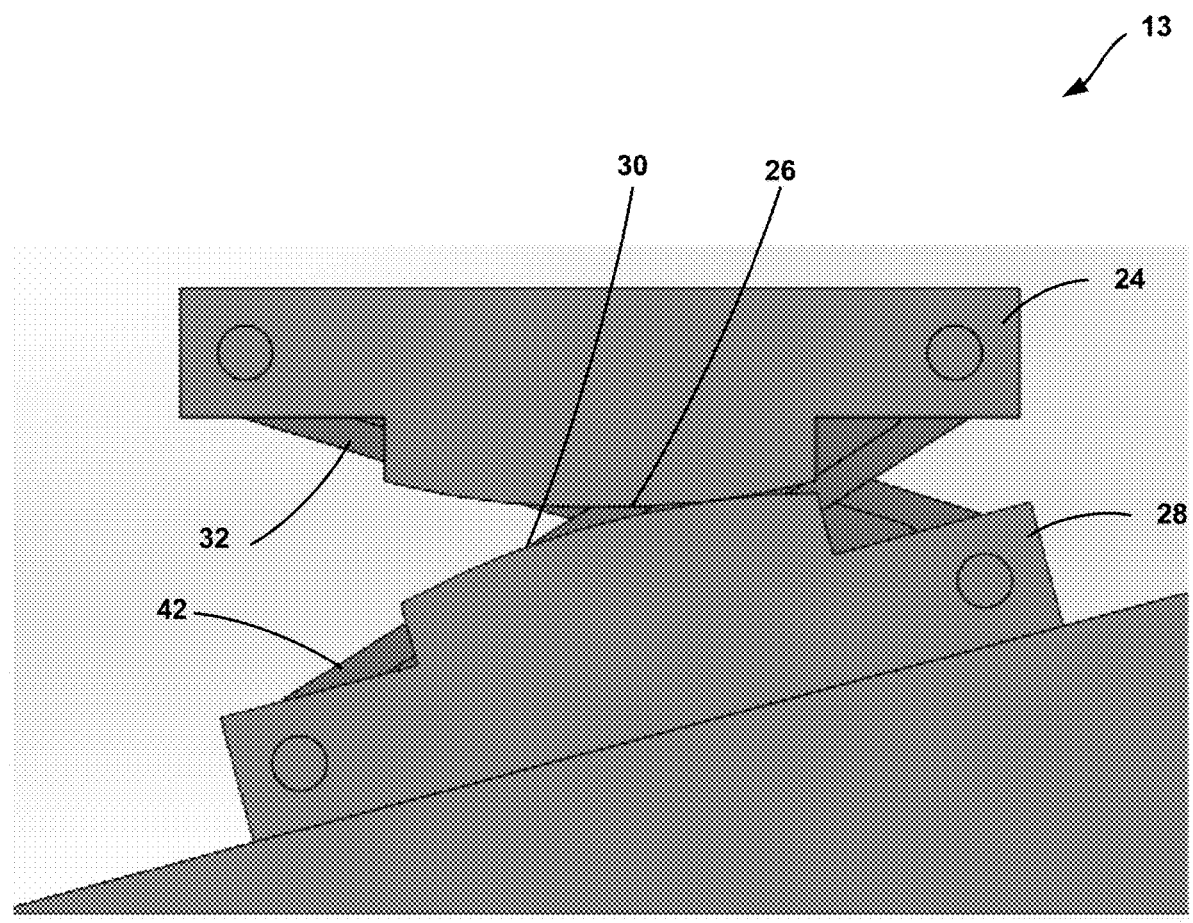
FIG. 6 shows another example linkage system on an incline, according to an example embodiment.

FIG. 6 shows another example linkage system 13 on a medial-lateral grade, according to an example embodiment. The linkage system 13 may be substantially the same as linkage system 11, with the exception of the second contact surface 30 of the first lower portion 28. As such, the linkage system 13 may be used as the first linkage system 12, the second linkage system 14, and/or the third linkage system. As shown in FIG. 6, the first contact surface 26 of the linkage system 13 comprises a convex surface, and the second contact surface 30 of the linkage system 13 also comprises a convex surface. As the base 18 and hindfoot pad 20 contacts uneven ground, the first lower portion 28 of the linkage system 13 rotate, and becomes parallel to the ground surface. At the same time, the first upper portion 24 of the linkage system 13 remains perpendicular to the prosthetic limb 22. As the first upper portion 24 rotates with respect to the first lower portion 28, the first contact surface 26 remains in contact with the second contact surface 60.

Thus, using one or more of the linkage systems described in FIGS. 5 and 6, the prosthetic device 10 may help individuals having poor balance and gait. For example, the ground may be even but the prosthetic device 10 may come in contact with the ground at an angle due to poor balance and gait of the user. If the prosthetic device 10 contacts the ground in the medial-lateral direction, the first lower portion 28 of the first linkage system 12 and the second linkage system 14 rotates, and becomes parallel to the ground surface, while the first upper portion 24 of the first linkage system 12 and the second linkage system 14 remains perpendicular to the prosthetic limb 22. In the embodiment including a third linkage system, if the prosthetic device 10 contacts the ground in a dorsiflexion or plantarflexion position, the third lower portion of the third linkage system may rotate, and become parallel to the inclined ground surface, while the third upper portion of the third linkage system may remain perpendicular to the prosthetic limb 22.

Figure 7:
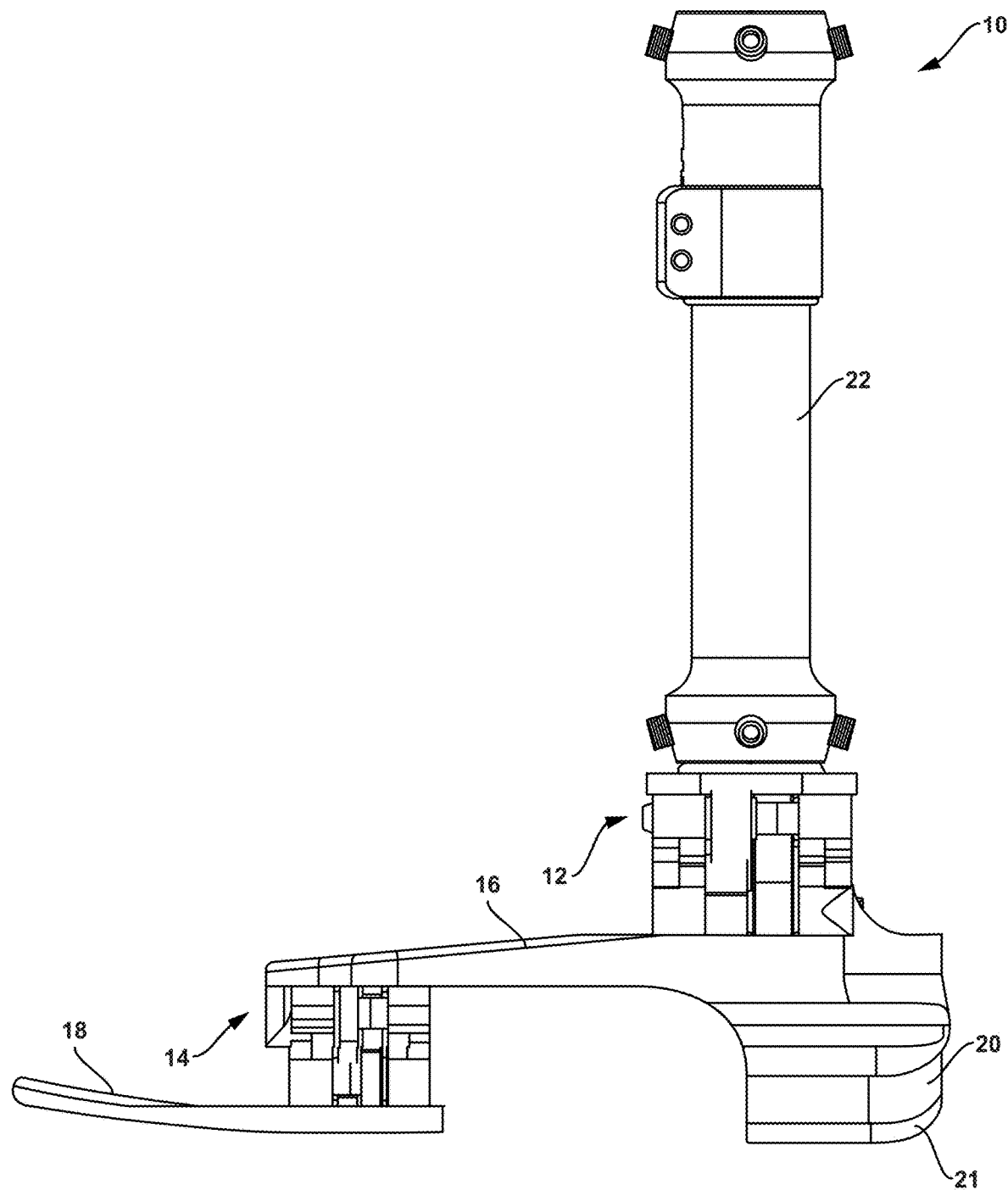
FIG. 7 is a side view of the prosthetic device, according to the example embodiment of FIG. 1.

FIG. 7 illustrates a side view of the prosthetic device 10, including the first linkage system 12, the second linkage system 14, the platform 16, the base 18, the hindfoot support 20, the hindfoot pad 21, and the prosthetic limb 22. FIG. 8 illustrates a rear view of the prosthetic device 10, including the first linkage system 12, the second linkage system 14, the hindfoot support 20, the hindfoot pad 21 and the prosthetic limb 22. Similarly, FIG. 9 illustrates a front view of the prosthetic device 10, including the first linkage system 12, the second linkage system 14, the platform 16, the base 18, and the prosthetic limb 22.

Figure 10:
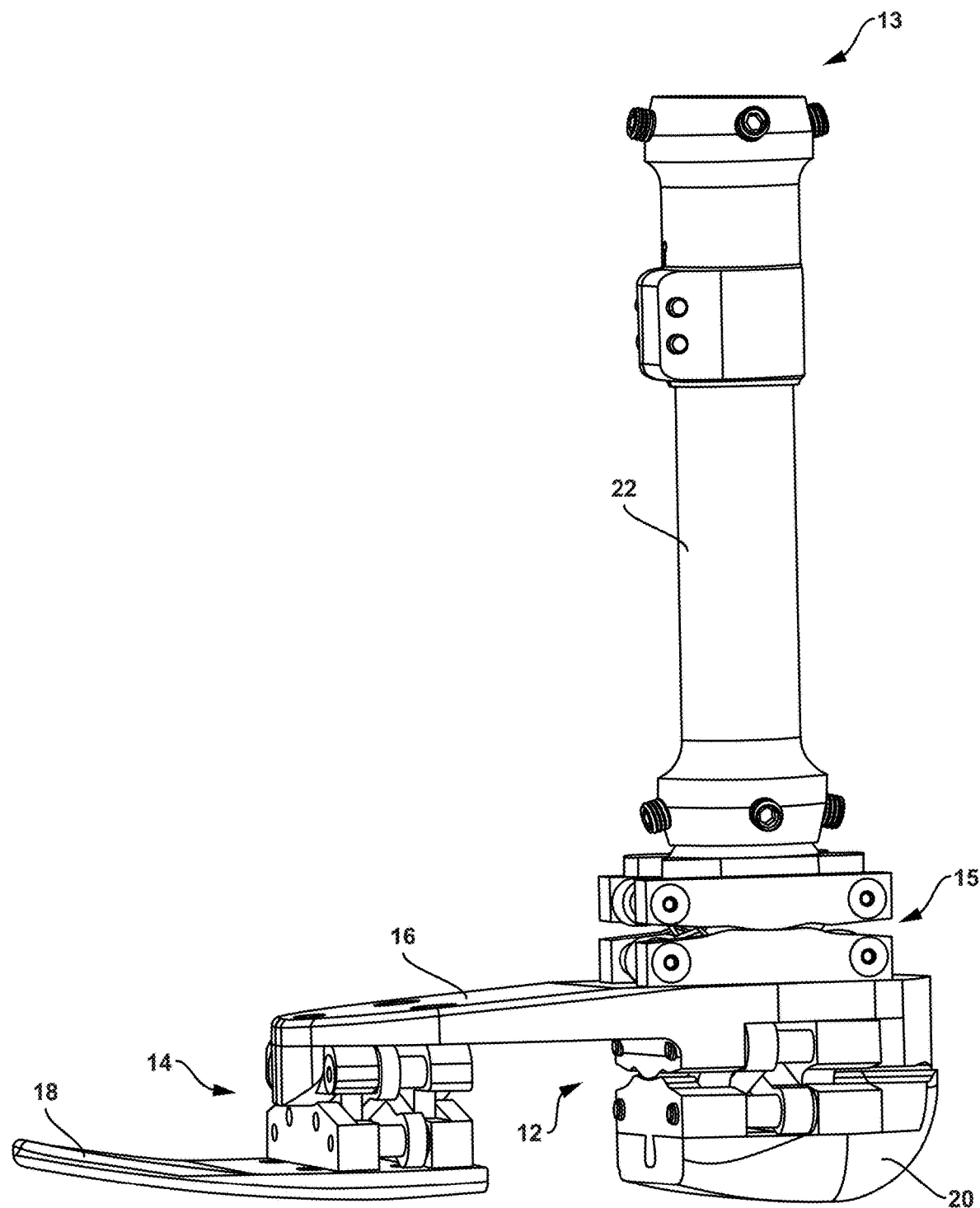
FIG. 10 is a perspective view of a prosthetic device, according to a second example embodiment.

FIG. 10 illustrates another prosthetic device 13 in accordance with another embodiment of the invention. As shown in FIG. 10, the prosthetic device 13 includes a first linkage system 12 and a second linkage system 14. The first linkage system 12 may be a hindfoot component of the prosthetic device 13, and the second linkage system 14 may be a forefoot component. The plane of rotation of the first linkage system 12 may be substantially parallel to the plane of rotation of the second linkage system 14. In other words, like components of the first linkage system 12 and the second linkage system 14 are facing the same direction, as shown in FIG. 10. The prosthetic device 13 may also include a platform 16 coupling the first linkage system 12 to the second linkage system 14. The prosthetic device 10 may further include a base 18 coupled to a lower portion of the second linkage system 14.

The prosthetic device 13 may further include a third linkage system 15 positioned between the platform 16 and the prosthetic limb 22. The third linkage system 15 may have a similar configuration to the first linkage system 12 and the second linkage system 14 (as described in relation to linkage system 11 in FIGS. 2-6). In particular, the third linkage system 15 may include (i) a third upper portion having a third contact surface, (ii) a third lower portion having a fourth contact surface, wherein the fourth contact surface contacts the third contact surface, (iii) a third tension bearing element with a first end pivotally coupled to a first end of the third lower portion and a second end pivotally coupled to a second end of the third upper portion, and (iv) a fourth tension bearing element with a first end pivotally coupled to a second end of the third lower portion and a second end pivotally coupled to a first end of the third upper portion. In such an example, the first upper portion 24 of the first linkage system 12 is coupled to the platform 16 and the third lower portion of the third linkage system is coupled to one of the platform 16 or the first upper portion 24 of the first linkage system 12.

In addition, the plane of rotation of the third linkage system 15 may be substantially perpendicular to the plane of rotation of the first linkage system 12 and the plane of rotation of the second linkage system 14. In particular, the plane of rotation of the third upper portion of the third linkage system 15 is perpendicular to the plane of rotation of the first upper portion of the first and second linkage systems. In such a configuration, the first linkage system 12 and the second linkage system 14 may enable medial-lateral movement, such as pronation and supination of the foot. The third linkage system 15 may enable dorsiflexion and plantar-flexion of the foot. While three linkage systems are described herein, any number of linkage systems similar to linkage system 11 may be added to the prosthetic device 10 to improve stability of the wearer.

In a configuration including the third linkage system 15, the prosthetic limb 22 may be coupled to the third upper portion of the third linkage system 15. A bottom portion of the prosthetic limb 22 may include a connector portion that is configured to mate with a connector portion positioned on a top surface of the third upper portion of the third linkage system. Other connection mechanisms are possible as well.

Figure 11:
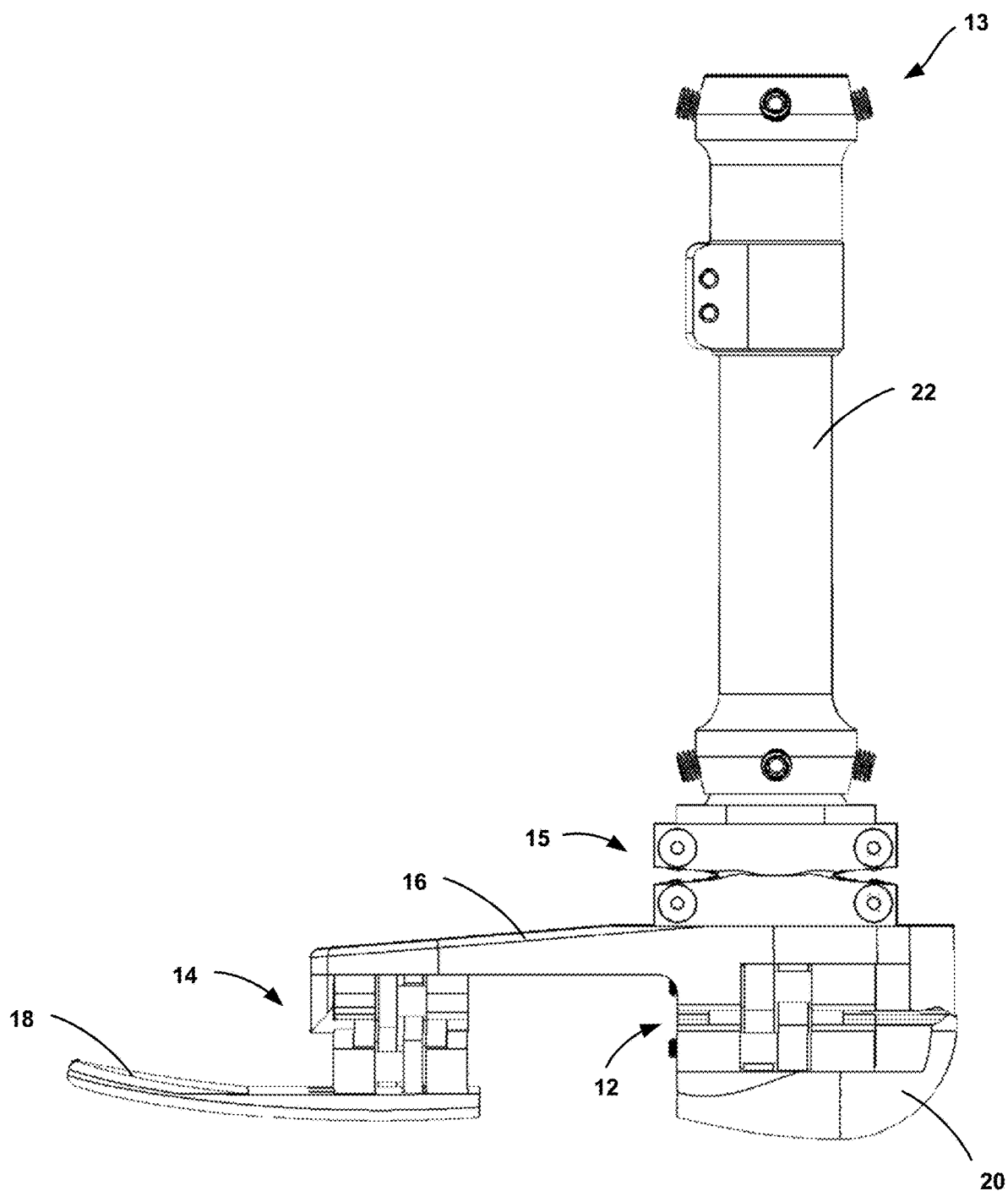
FIG. 11 is a side view of the prosthetic device, according to the example embodiment of FIG. 10.
Figure 12:
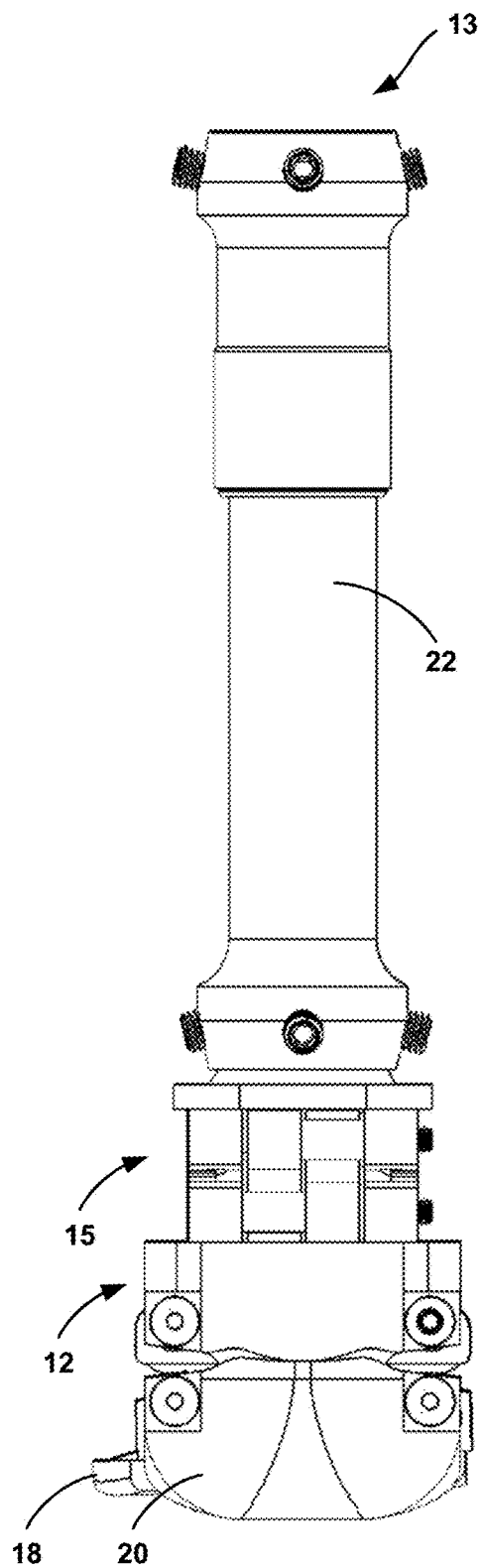
FIG. 12 is a rear view of the prosthetic device, according to the example embodiment of FIG. 10.
Figure 13:
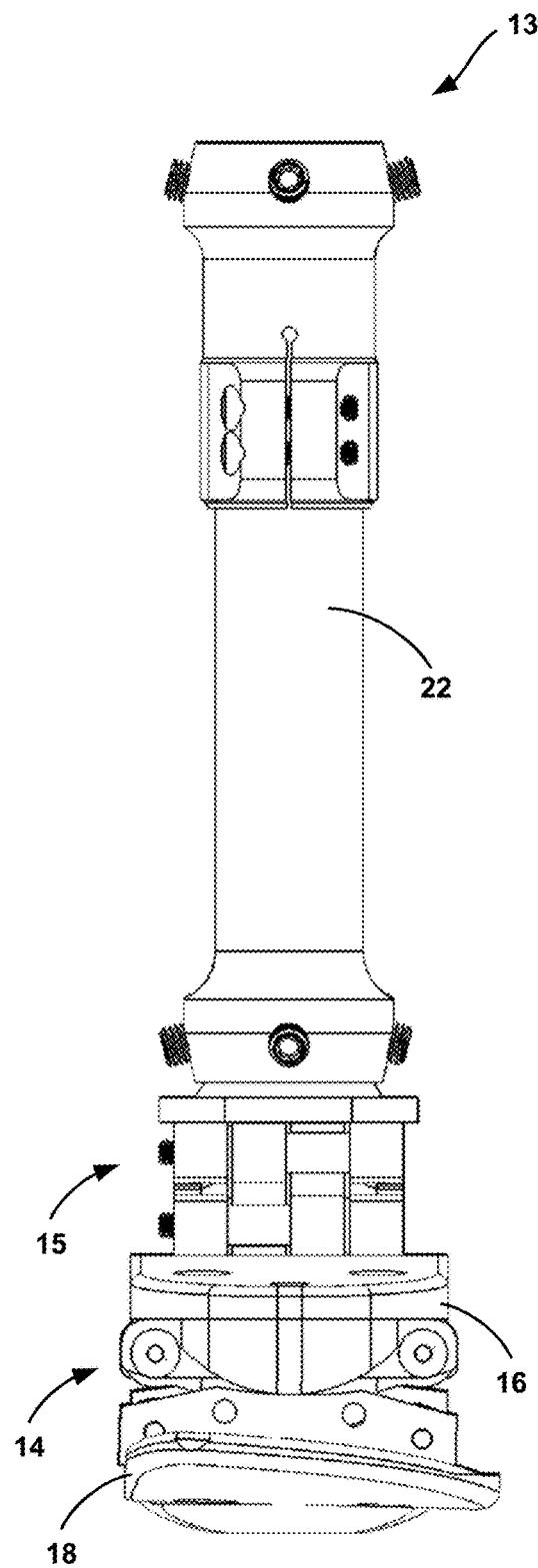
FIG. 13 is a front view of the prosthetic device, according to the example embodiment of FIG. 10.

FIG. 11 illustrates a side view of the prosthetic device 13, including the first linkage system 12, the second linkage system 14, the third linkage system 15, the platform 16, the base 18, the hindfoot support 20, and the prosthetic limb 22. FIG. 12 illustrates a rear view of the prosthetic device 13, including the first linkage system 12, the third linkage system 15, the base 18, the hindfoot support 20, and the prosthetic limb 22. Similarly, FIG. 13 illustrates a front view of the prosthetic device 13, including the second linkage system 14, the third linkage system 15, the platform 16, the base 18, and the prosthetic limb 22.

Figure 14:
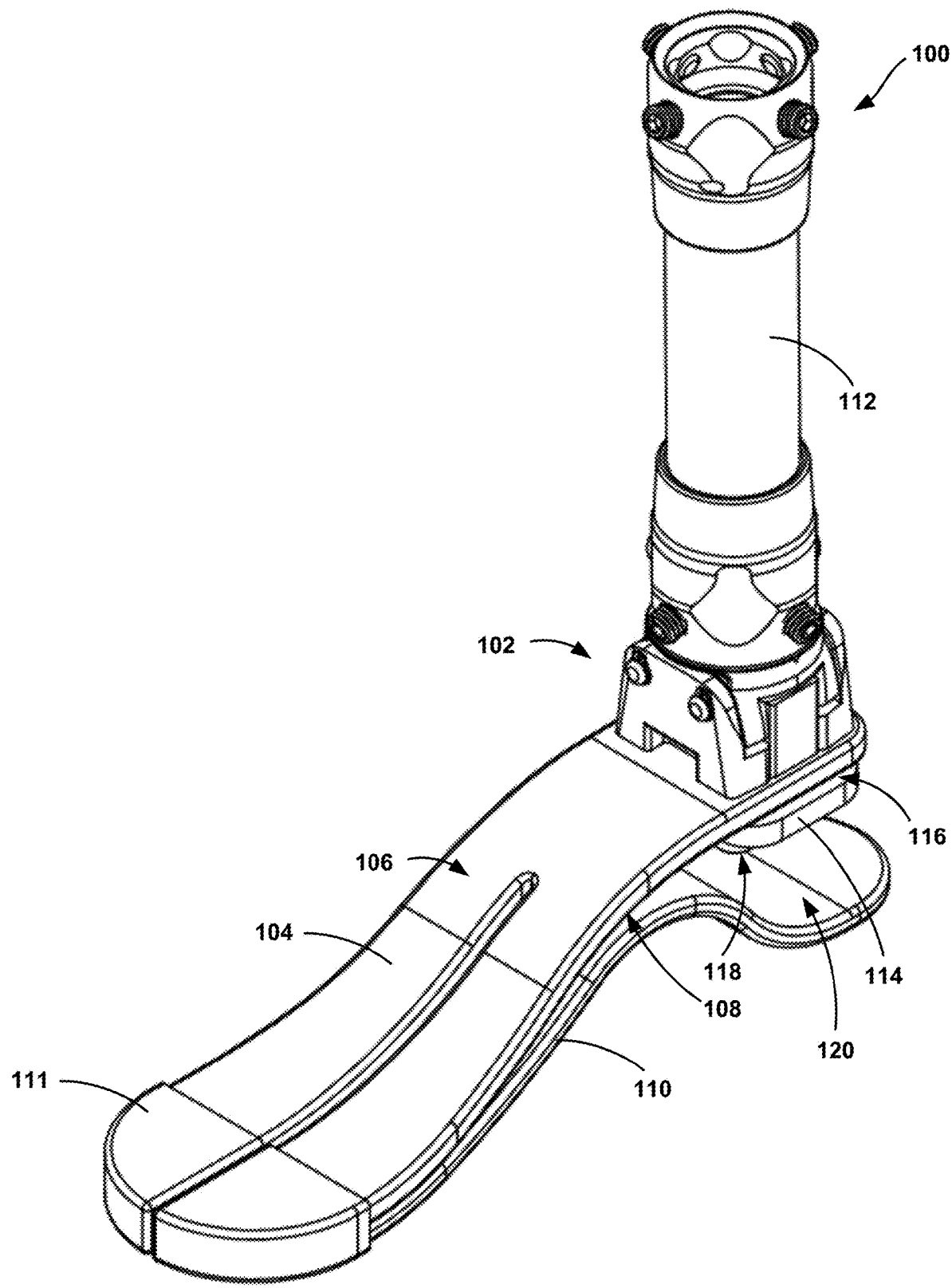
FIG. 14 is a perspective view of a prosthetic foot device, according to an example embodiment.

FIG. 14 illustrates another example prosthetic foot device 100. As shown in FIG. 14, the prosthetic foot device 100 includes a linkage system 102, a platform 104 having a top surface 106 and a bottom surface 108, and a base 110 coupled to the bottom surface 108 of the platform 104. As shown in FIG. 14, the platform 104 and the base 110 may be coupled to one another via a toe cap 111. Further, as shown in FIG. 14, a portion the platform 104 and/or the base 110 may include a slot positioned therein. Such a slot may provide lateral flexibility when the prosthetic foot device 100 is in use. The platform 104 may include carbon fiber, a fiber-reinforced composite, a high density nylon material, polyoxymethylene, epoxy, or combinations thereof, amongst other possibilities. Similarly, the base 110 may include carbon fiber, a fiber-reinforced composite, a high density nylon material, polyoxymethylene, epoxy, or combinations thereof, among other possibilities. In one example, the platform 104 and the base 110 may form a flexible bridging platform configured to mimic a tarsal joint (midfoot) of a normal foot to supply a balance of rigidity and spring to the foot function. As weight moves from hindfoot to forefoot, the platform 104 and base 110 accommodates unevenness between the front and back ground level, as well as the angle of the user's leg relative to the floor. As the wearer of the prosthetic foot device 100 shifts their weight forward, the platform 104 and base 110 may act as a springboard propelling the wearer forward in bipedal motion.

As shown in FIG. 14, a prosthetic limb 112, such as a shank, may be coupled to the platform 104, in a position above the linkage system 102. A bottom portion of the prosthetic limb 112 may include a connector portion that is configured to mate with a connector portion positioned on the platform 104. In another embodiment, the prosthetic foot device 100 may be coupled to a robotic device, such as a leg of a legged robotic device. Other connection mechanisms are possible as well. In one example, the prosthetic foot device 100 further includes a housing positioned around the prosthetic foot device 100. For example, the housing may be a shoe that encompasses the prosthetic foot device 100. In another example, the housing may be shaped like a human foot. Other examples are possible as well.

The length-to-height ratio of the linkage system 102 may vary. In one example, the length-to-height ratio may be greater than 1.5:1. For example, the length-to-height ratio of the linkage system may be 2:1, or 3:1. It may be desirable to keep the center of rotation of the linkage system 102 relatively low, so as to keep the center of rotation within the base of support at the maximal angular position. The physical size of the linkage system 102 is scalable within the desired length-to-height ratio.

As shown in FIG. 14, the prosthetic foot device 100 may further include a hindfoot support 114 positioned between the platform 104 and the base 110. In particular, the hindfoot support 114 includes an upper surface 116 coupled to the bottom surface 108 of the platform 104 and a bottom surface 118 coupled to an upper surface 120 of the base 110. In another example, the upper surface 116 of the hindfoot support 114 is coupled to the bottom surface 108 of the platform 104, and the bottom surface 118 of the hindfoot support is coupled to a spring mechanism. Other arrangements are possible as well.

Figure 15:
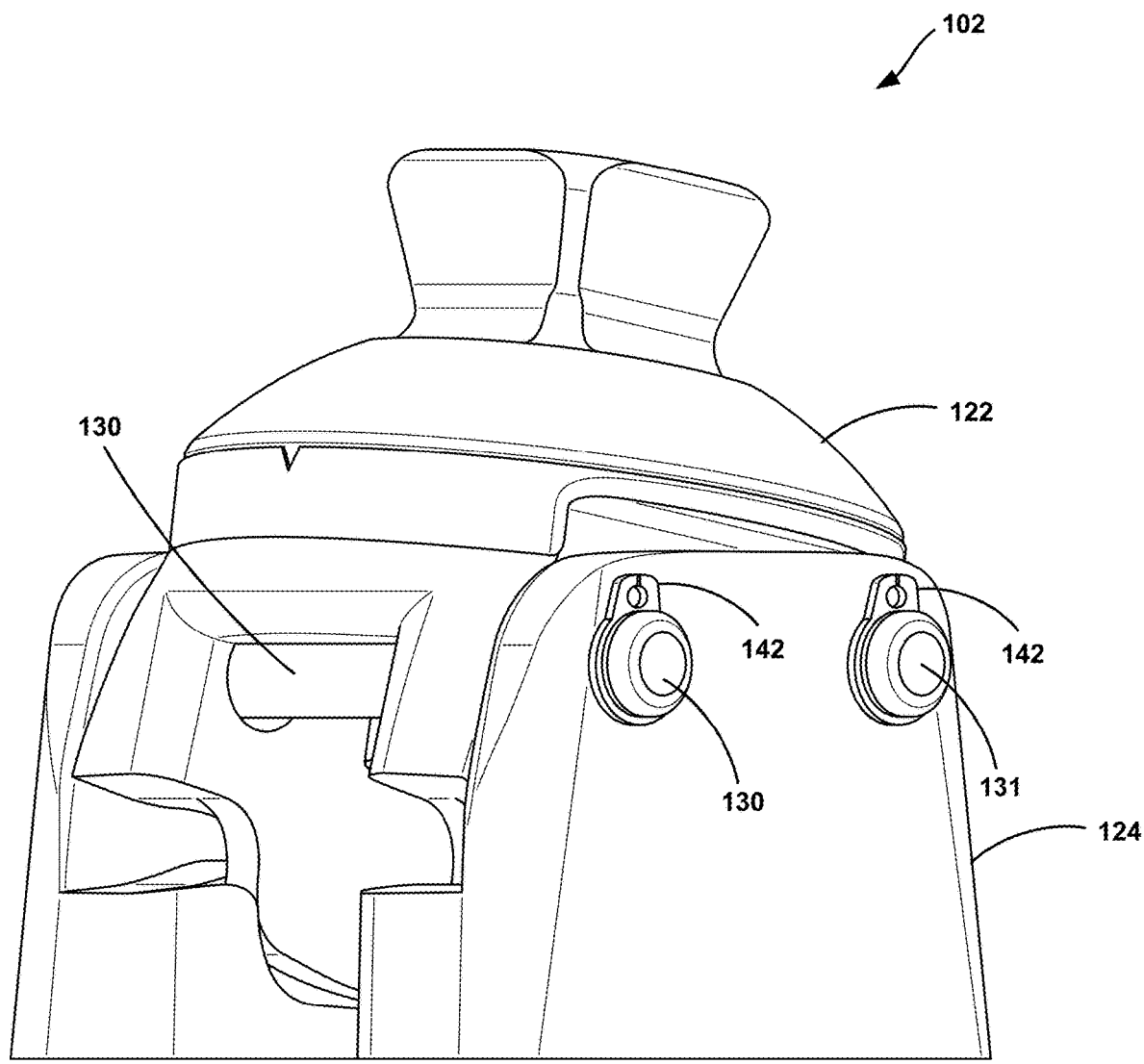
FIG. 15 is a perspective view of a linkage system, according to the example embodiment of FIG. 14.
Figure 16:
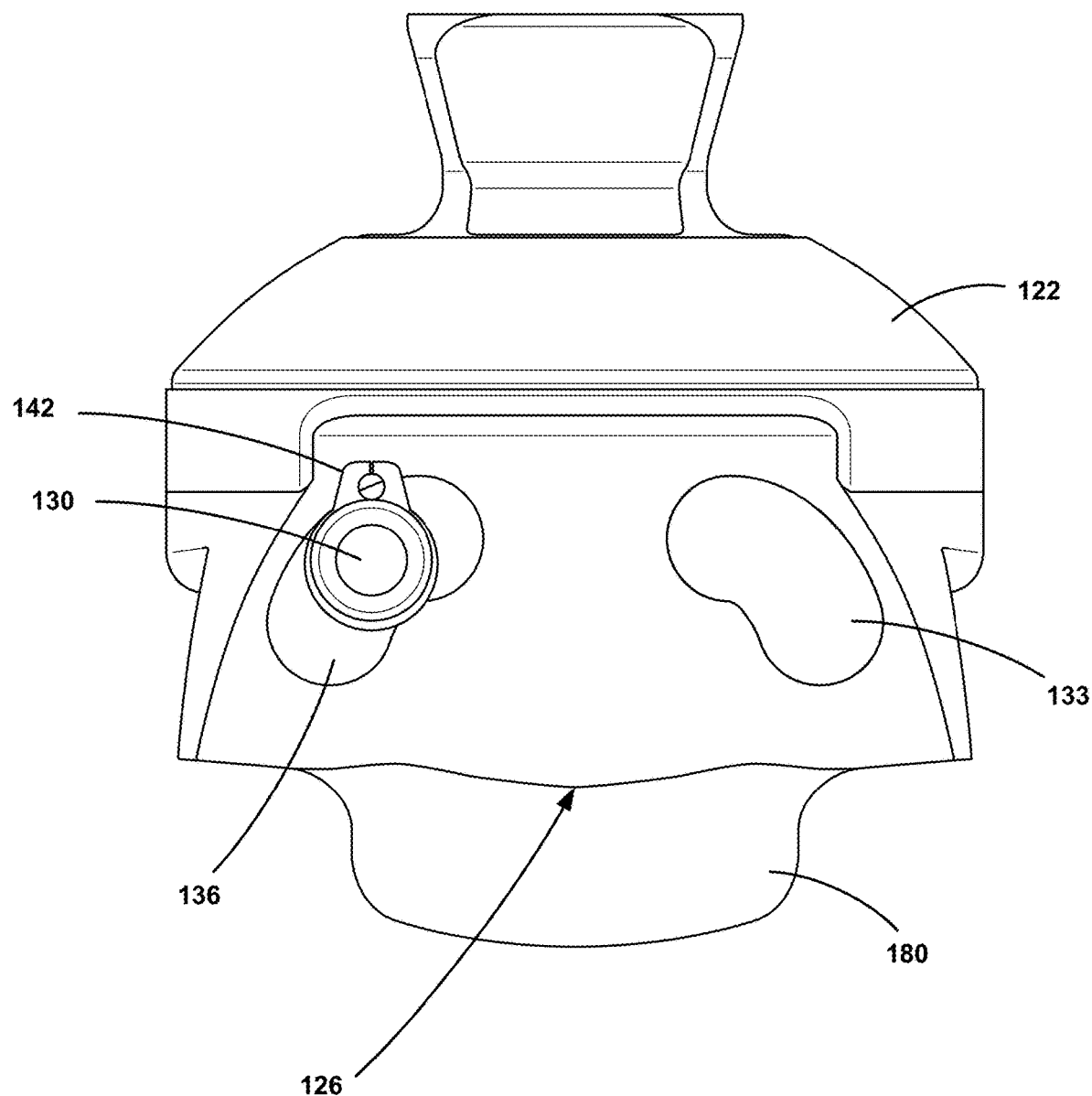
FIG. 16 is a side view of an upper portion of the linkage system, according to the example embodiment of FIG. 15.
Figure 17:
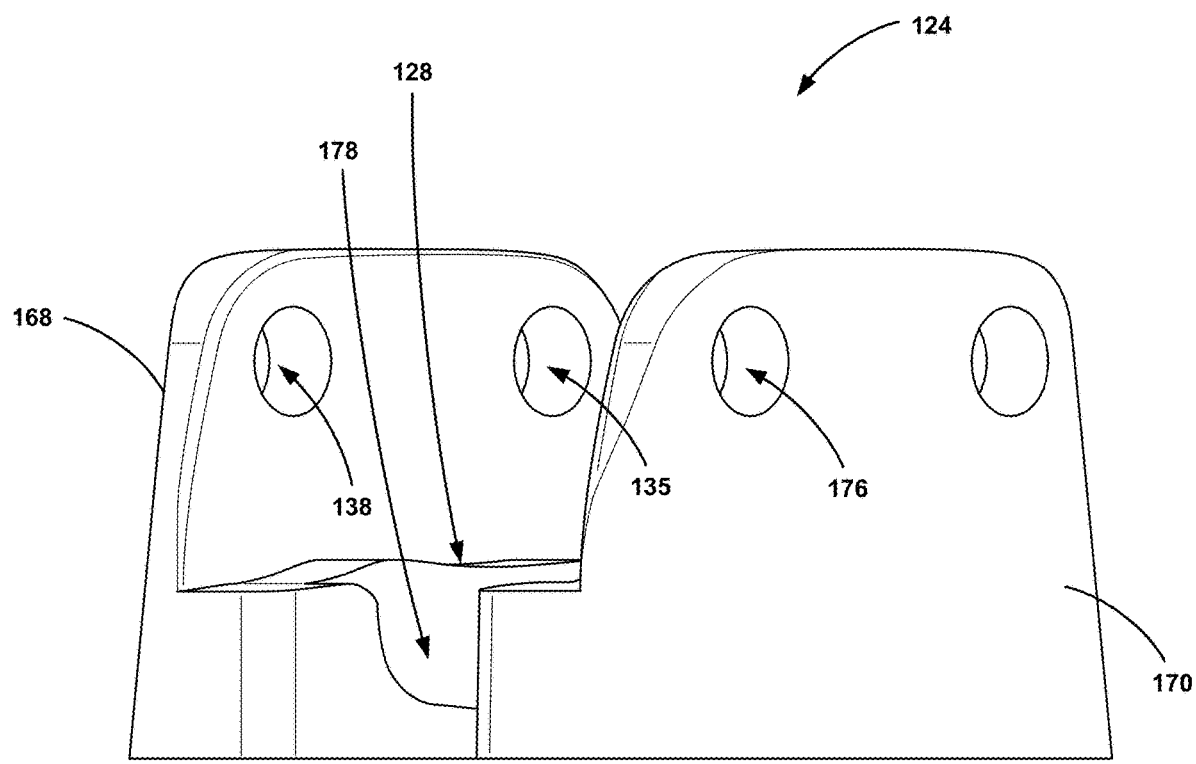
FIG. 17 is a perspective view of the lower portion of the linkage system, according to the example embodiment of FIG. 15.
Figure 18:
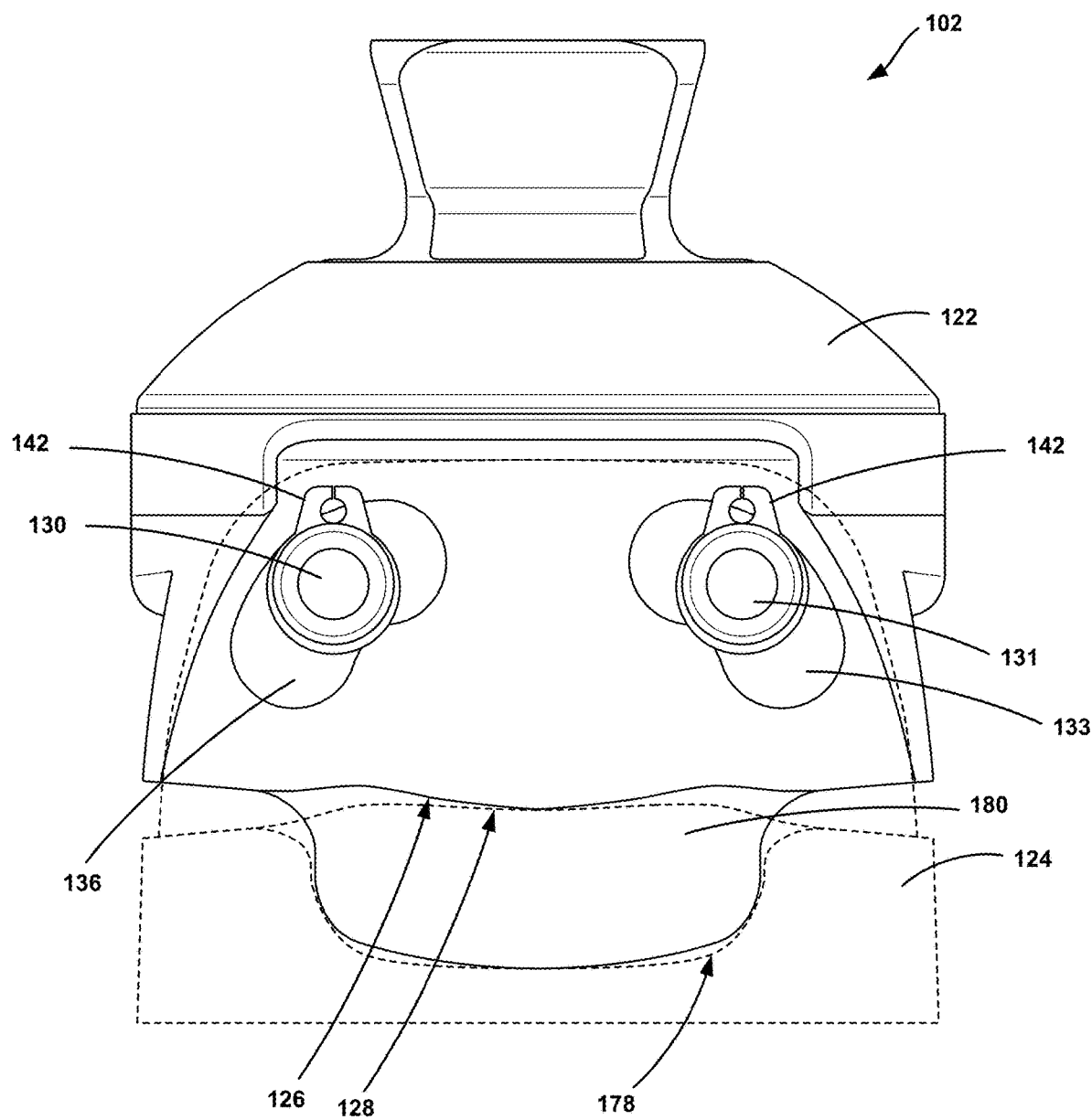
FIG. 18 is a side view of the linkage system in a neutral position, according to the example embodiment of FIG. 15.
Figure 19:
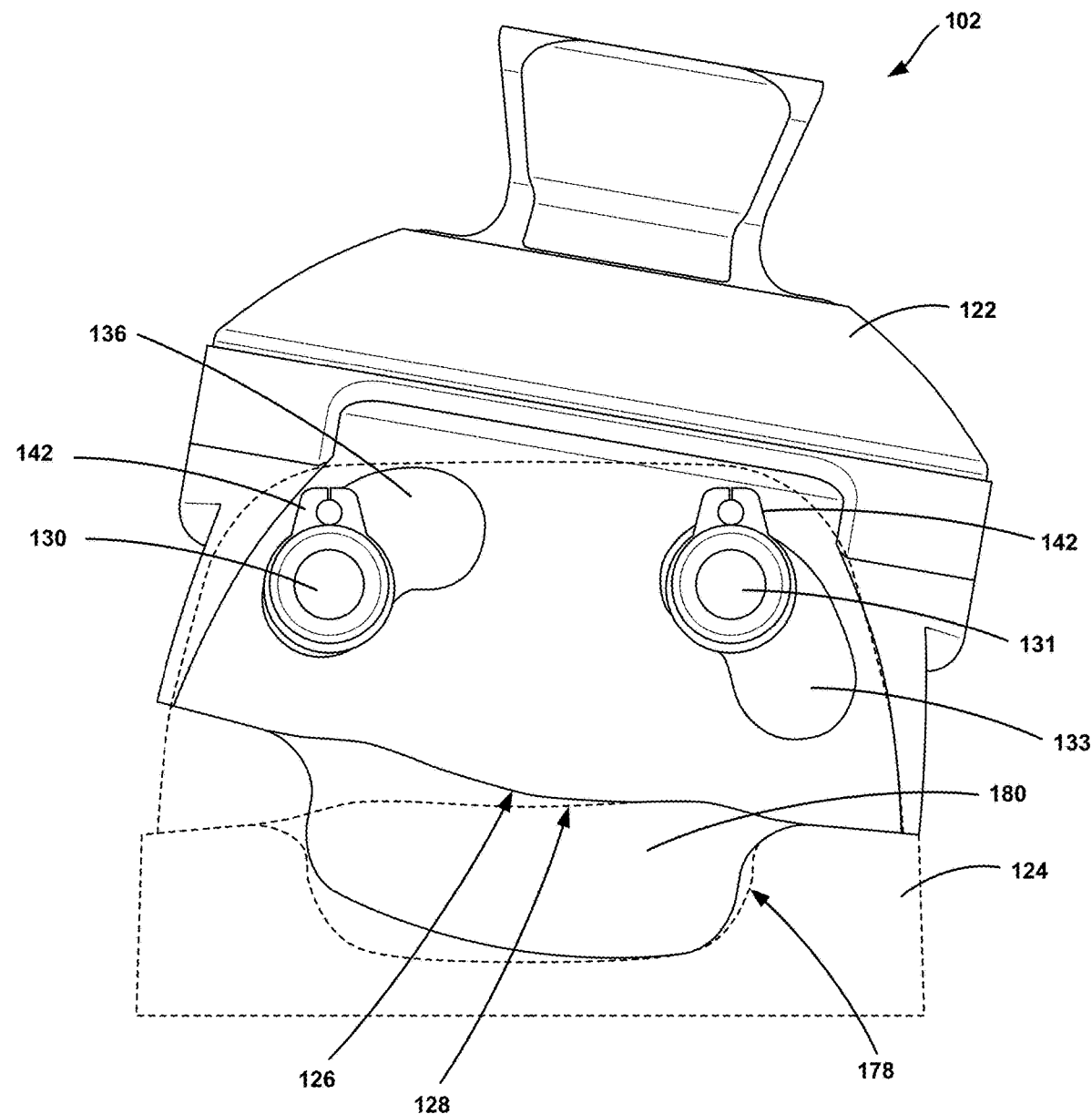
FIG. 19 is a side view of the linkage system in a rotated position, according to the example embodiment of FIG. 15.

FIG. 15 illustrates an example embodiment of the linkage system 102. The linkage system 102 may be a component of the prosthetic foot device 100, as shown in FIG. 14, or it may be a standalone component that can be added to a variety of prosthetic designs. As shown in FIG. 15, the linkage system 102 may include an upper portion 122 and a lower portion 124. The upper portion 122 is shown in isolation in FIG. 16, and the lower portion 124 is shown in isolation in FIG. 17. As shown in FIG. 16, the upper portion 122 includes a first contact surface 126. As shown in FIG. 17, the lower portion 124 includes a second contact surface 128. The second contact surface 128 is configured to contact the first contact surface 126, as shown in FIGS. 18 and 19. In particular, FIG. 18 illustrates the linkage system 102 in a neutral state, while FIG. 19 illustrates the linkage system 102 with the upper portion 122 rotated with respect to the lower portion 124. The assembly of pin 130 with through-holes 136 and 138 helps to resist tension forces while the second contact surface 128 helps in compression. Although FIG. 19 illustrates the upper portion 122 rotating with respect to the lower portion 124, in another embodiment the lower portion 124 is configured to rotate with respect to the upper portion 122, as discussed in additional detail below.

Figure 20:
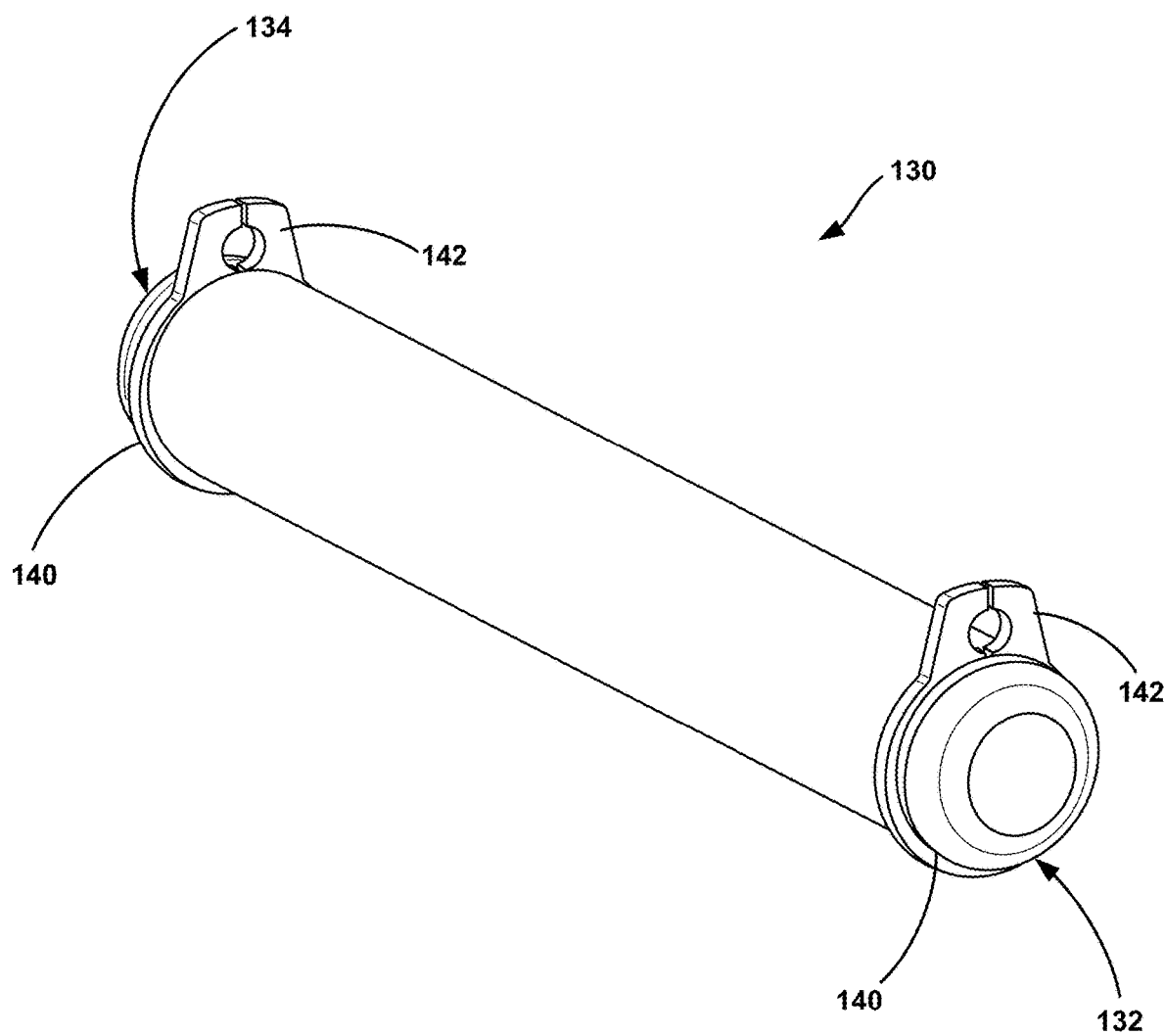
FIG. 20 is a perspective view of a pin of the linkage system, according to the example embodiment of FIG. 15.

The linkage system 102 may also include a pin 130 having a first end 132 and a second end 134, as shown in FIG. 20. As shown in the Figures, the pin 130 is positioned through a first through-hole 136 in the upper portion 122 and further through a second through-hole 138 in the lower portion 124 such that the upper portion 122 is rotatably coupled to the lower portion 124 via the pin 130. As shown in FIG. 20, in one example each of the first end 132 and the second end 134 of the pin 130 includes a groove 140 configured to receive a retaining ring 142 that locks the pin 130 in position. As shown in FIG. 15, the pin 130 comprises a first pin, and the prosthetic foot device 100 further includes a second pin 131 having a first end and a second end. The second pin 131 is positioned through a third through-hole 133 in the upper portion 122 and further through a fourth through-hole 135 in the lower portion 124, as discussed in additional detail below. Additional pins are possible as well. In one example, one or more of the first through-hole 136 and the second through-hole 138 includes a bearing configured to receive the pin 130, such that the pin 130 can roll during motion of the linkage system 102.

In one example, as shown in FIGS. 18 and 19, the first contact surface 126 of the linkage system 102 comprises a convex surface, and the second contact surface 128 of the linkage system 102 comprises a concave surface. In such an example, a contact between the first contact surface 126 and the second contact surface 128 of the linkage system 102 comprises an instantaneous center of rotation of the upper portion 122 with respect to the lower portion 124. In another example, first contact surface 126 of the linkage system 102 comprises a convex surface, and the second contact surface 128 of the linkage system 102 also comprises a convex surface.

In one example, the first contact surface 126 comprises a first material, and the second contact surface 128 comprises a second material that is different than the first material. In one particular example, the first contact surface 126 comprises fiber reinforced composite, aluminum, stainless steel, or titanium, while the second contact surface comprises a polymer such as polyoxymethylene, polyethylene, or nylon. In another example, the first contact surface 126 comprises a polymer such as polyoxymethylene, polyethylene, or nylon, while the second contact surface 128 comprises fiber reinforced composite, aluminum, stainless steel, or titanium. Other examples are possible as well. In one example, the entire upper portion 122 may comprise the materials described above for the first contact surface 126. In another example, the upper portion 122 is coated with a different material at the first contact surface 126, such that the material at the first contact surface 126 is different than the material of the rest of the upper portion 122. Similarly, in one example the entire lower portion 124 may comprise the materials described above for the second contact surface 128. In another example, the lower portion 124 is coated with a different material at the second contact surface 128, such that the material at the second contact surface 128 is different than the material of the rest of the lower portion 124.

Figure 21:
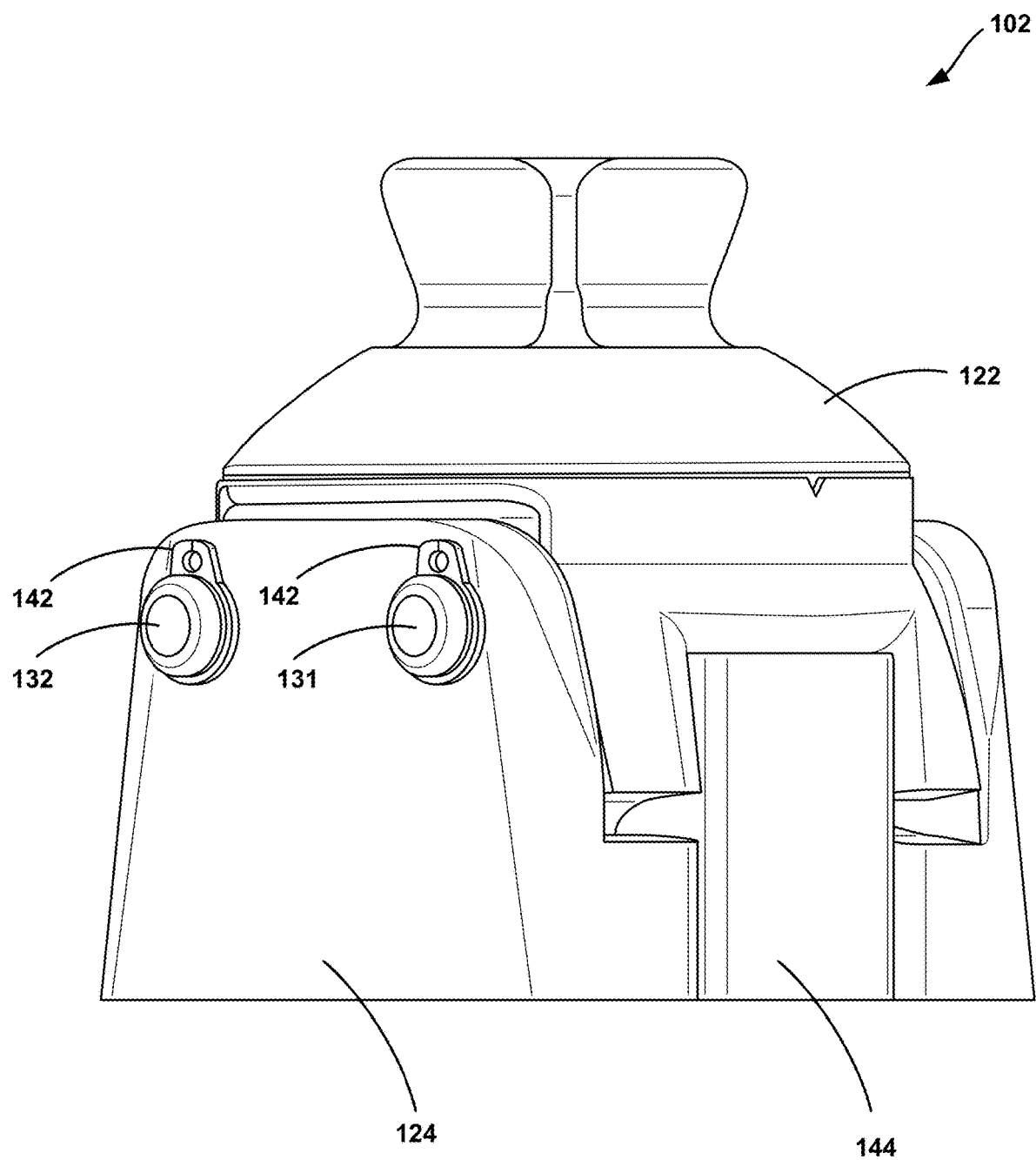
FIG. 21 is a perspective view of a linkage system including an elastic material, according to an example embodiment.

In one embodiment, the linkage system 102 includes at least one spring mechanism configured to return the linkage system 102 to a position of repose when the prosthetic foot device 100 is unweighted. In one example, the spring mechanism comprises an elastic material 144 disposed between the upper portion 122 and the lower portion 124, as shown in FIG. 21. The elastic material 144 may include polyurethane or rubber, as a non-limiting example. In another example, the spring mechanism comprises an actuator disposed between the upper portion 122 and the lower portion 124. The at least one spring mechanism may be configured to transition the linkage system 102 from a weighted height to an unweighted height. For example, in operation a wearer of the prosthetic foot device 100 may step on an inclined surface at an angle to the incline, as discussed above in more detail below in relation to FIGS. 5 and 6. In such a case, on one side of the linkage system 102, the upper portion 122 moves closer to the lower portion 124. At the same time on the opposite side of the linkage system 102, the upper portion 122 moves further away from the lower portion 124. As the wearer lifts the prosthetic foot device 100 off of the inclined surface, the at least one spring mechanism may return or assist with returning the linkage system 102 to a position of repose before the wearer places the foot back on the ground.

Further, the at least one spring mechanism may be used to modify rotational properties of the upper portion 122 with respect to the lower portion 124. For example, the elastic material 144 may provide a dampening effect to smooth out movements of the upper portion 122 with respect to the lower portion 124. Further, the elastic material 144 may be removably positioned between the upper portion 122 and the lower portion 124. As such, elastic materials of varying stiffness may be positioned between the upper portion 122 and the lower portion 124. For example, a heavier individual may benefit from having an elastic material 144 with more stiffness, while a lighter individual may benefit from having an elastic material 144 with less stiffness. Further, the type of elastic material 144 may be selected based on the activities in which the user of the prosthetic foot device 100 intents to partake.

The linkage system 102 may have a defined maximum rotation to better mimic the corresponding joint of a human foot. In one example, the at least one spring mechanism may be used to define the maximum rotation for the linkage system. In another example, the structure of the linkage itself may define the maximum angle of rotation. In one example, a maximum angle between the upper portion 122 of the linkage system 102 and the lower portion 124 of the linkage system 102 is between about ten and about forty-five degrees.

In one example, the first through-hole 136 in the upper portion 122 comprises a curved slot, as shown in FIG. 16, and the second through-hole 138 in the lower portion 124 comprises a substantially cylindrical through-hole, as shown in FIG. 17. The path of the slot matches the motion of the second contact surface 128. The bottom half of the slot surface will remain in contact with the pin 130 to resists tension forces. In such an example, the upper portion 122 is configured to rotate with respect to the bottom portion 124. In another example, the first through-hole 136 in the upper portion 122 comprises a substantially cylindrical through-hole, and the second through-hole 138 in the lower portion 124 comprises a curved slot. In such an example, the lower portion 124 is configured to rotate with respect to the upper portion 122.

The upper portion 122 of the linkage system 102 and the bottom portion 124 of the linkage system 102 may take a variety of forms. In one example, the upper portion 122 and the lower portion 124 are both substantially solid. In such an example, the first through-hole 136 in the upper portion 122 extends from a first side of the upper portion 122 to a second side of the upper portion 122, and the second through-hole 138 in the lower portion 124 extends from a first side of the lower portion 124 to a second side of the lower portion 124.

Figure 22:
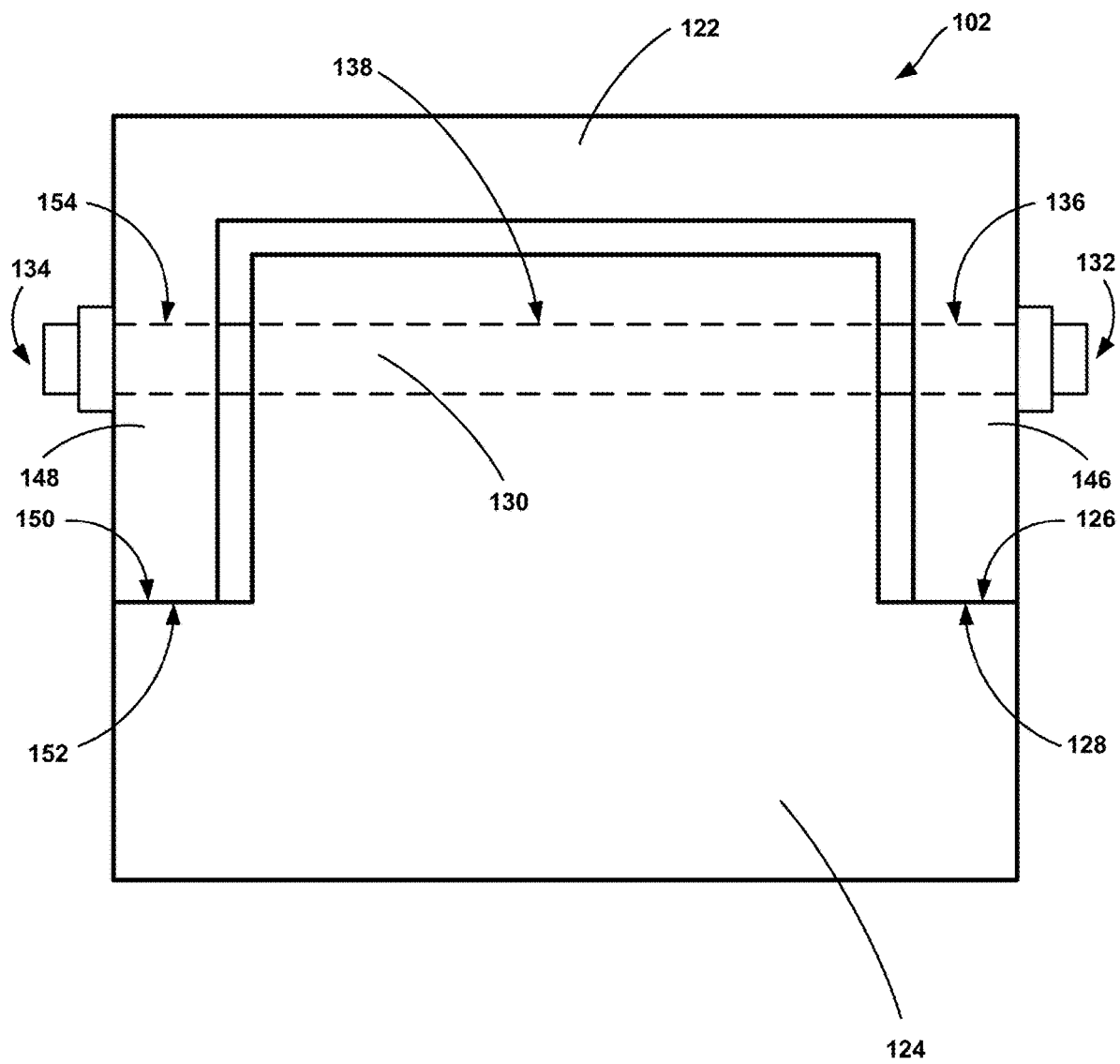
FIG. 22 is a side view of an example linkage system, according to an example embodiment.

In another example, as shown in FIG. 22, the lower portion 124 is substantially solid. In such an example, the second through-hole 138 in the lower portion 124 extends from a first side of the lower portion 124 to a second side of the lower portion 124. Further, in such an example, the upper portion 122 further comprises a first sidewall 146 spaced apart from a second sidewall 148. The first sidewall 146 includes the first contact surface 126 and the second sidewall 148 includes a third contact surface 150. In such an example, the second contact surface 128 of the lower portion 124 is configured to contact the first contact surface 126 and the third contact surface 150 of the upper portion 122 is configured to contact a fourth contact surface 152 of the lower portion 124. As shown in FIG. 22, the pin 130 is positioned through the second through-hole 138 in the lower portion 124. Further, the first end 132 of the pin 130 is positioned through the first through-hole 136 in the first sidewall 146 of the upper portion 122 and the second end 134 of the pin 130 is positioned through a third through-hole 154 in the second sidewall 148 of the upper portion 122 such that the upper portion 122 is rotatably coupled to the lower portion 124 via the pin 130.

Figure 23:
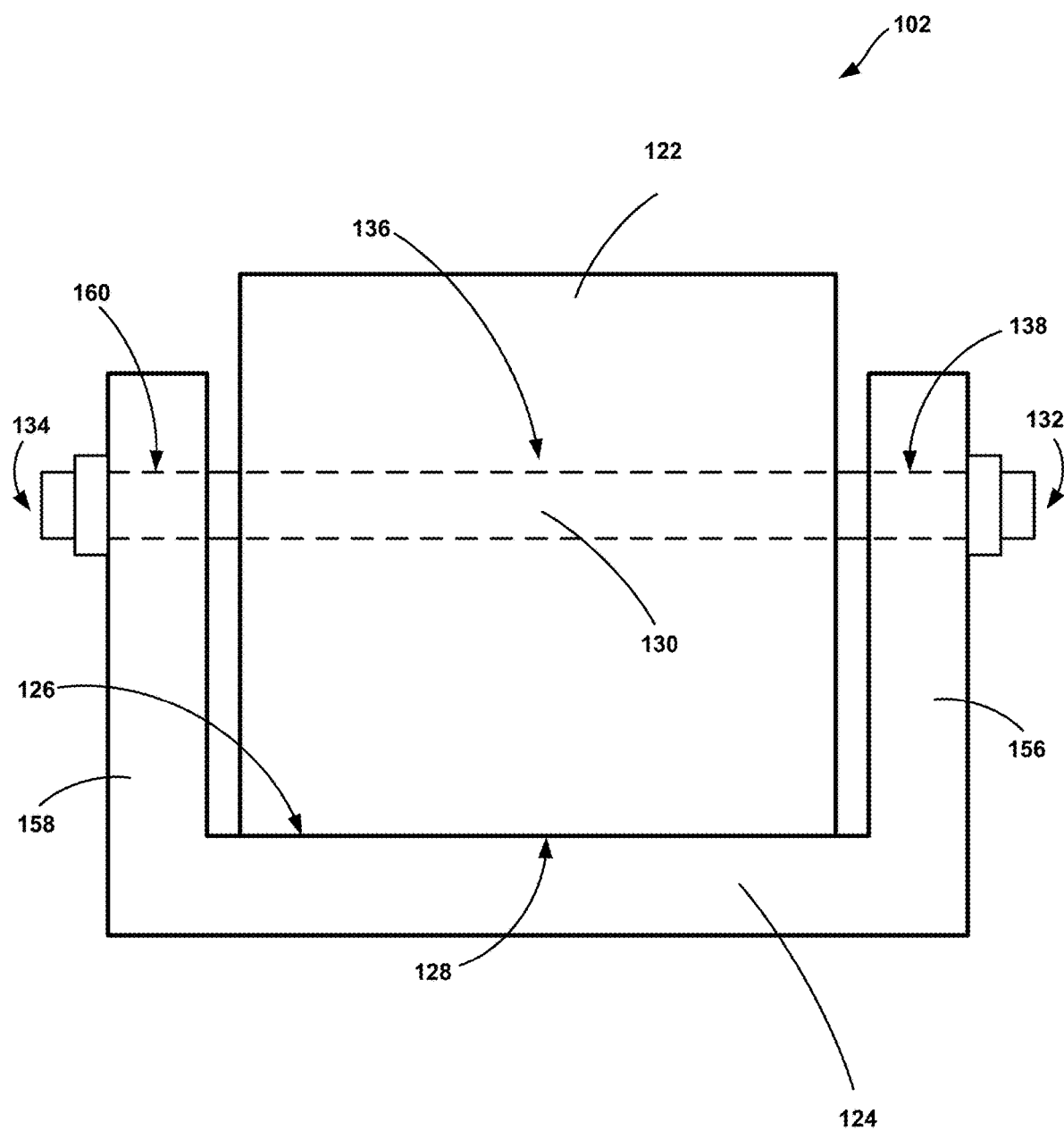
FIG. 23 is a side view of an example linkage system, according to an example embodiment.

In another example, as shown in FIG. 23, the upper portion is substantially solid. In such an example, the first through-hole 136 in the upper portion 122 extends from a first side of the upper portion 122 to a second side of the upper portion 122. Further, in such an example, the lower portion 124 further comprises a third sidewall 156 spaced apart from a fourth sidewall 158. The first contact surface 126 of the upper portion 122 is configured to contact the second contact surface 128 of the lower portion 124, as shown in FIG. 23. The pin 130 is positioned through the first through-hole 136 in the upper portion 122. Further, the first end 132 of the pin 130 is positioned through the second through-hole 138 in the third sidewall 156 of the lower portion 124 and the second end 134 of the pin 130 is positioned through a fourth through-hole 160 in the fourth sidewall 158 of the lower portion 124 such that the upper portion 122 is rotatably coupled to the lower portion 124 via the pin 130.

Figure 24:
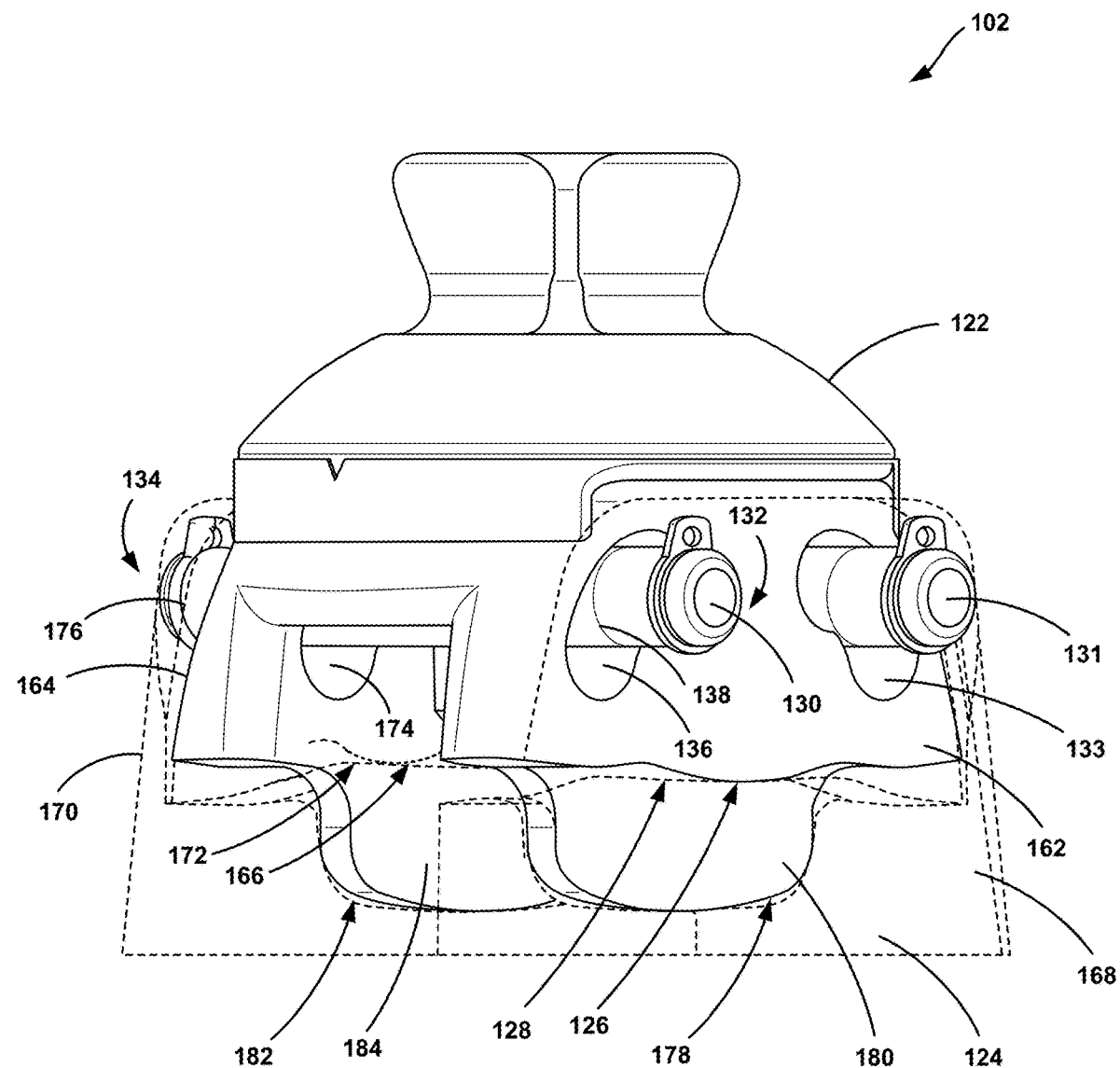
FIG. 24 is a perspective view of an example linkage system, according to an example embodiment.

In yet another example, as shown in FIG. 24, the upper portion 122 further comprises a first sidewall 162 spaced apart from a second sidewall 164. The first sidewall 162 includes the first contact surface 126 and the second sidewall 164 includes a third contact surface 166. The lower portion 124 further comprises a third sidewall 168 spaced apart from a fourth sidewall 170. The third sidewall 168 includes the second contact surface 128 and the fourth sidewall 170 includes a fourth contact surface 172. The first contact surface 126 of the upper portion 122 is configured to contact the second contact surface 128 of the lower portion 124, and the third contact surface 166 of the upper portion 122 is configured to contact the fourth contact surface 172 of the lower portion 124. The first end 132 of the pin 130 is positioned through the first through-hole 136 in the first sidewall 162 of the upper portion 122 and further through the second through-hole 138 in the third sidewall 168 of the lower portion 124. The second end 134 of the pin 130 is positioned through a third through-hole 174 in the second sidewall 164 of the upper portion 122 and further through a fourth through-hole 176 in the fourth sidewall 170 of the lower portion 124 such that the upper portion 122 is rotatably coupled to the lower portion 124 via the pin 130. As shown in FIG. 24, a second pin 131 may also be included, as discussed in additional detail above.

In one example, as shown in FIG. 24, the third sidewall 168 of the lower portion 124 includes a first cutout 178 configured to receive a first protrusion 180 of the first sidewall 162 of the upper portion 122, and the fourth sidewall 170 of the lower portion 124 includes a second cutout 182 configured to receive a second protrusion 184 of the second sidewall 164 of the upper portion 122. In one example, the third sidewall 168 of the lower portion 124 and the fourth sidewall 170 of the lower portion 124 are separate components that are individually coupled to the platform or the base, and the first sidewall 162 of the upper portion 122 and the second sidewall 164 of the upper portion 122 are connected to thereby comprise a single component. The third sidewall 168 of the lower portion 124 and the fourth sidewall 170 of the lower portion 124 are coupled to the platform 104 such that they remain perpendicular to the platform 104 when the prosthetic foot device 100 is in use. The third sidewall 168 of the lower portion 124 and the fourth sidewall 170 of the lower portion 124 help resists torques applied to the prosthetic foot device 100.

In another example, the linkage system 102 may comprise a first linkage system, and the prosthetic foot device 100 may further include a second linkage system that includes all of the components of the linkage system 102 as described above. Such an arrangement may be similar to the embodiment shown in FIG. 1, with the linkage system 102 replacing the first linkage system 12 and the second linkage system replacing the second linkage system 14. In such an example, linkage system 102 may be an ankle linkage component of the prosthetic foot device 100, and the second linkage system may be a forefoot linkage component. The plane of rotation of the first linkage system 102 may be substantially parallel to the plane of rotation of the second linkage system. In other words, like components of the first linkage system 102 and the second linkage system are facing the same direction. The prosthetic foot device 100 may also include a platform 104 having a top surface 106 and a bottom surface 108, as discussed above. The top surface 104 of the platform 104 is coupled to the lower portion of the first linkage system, and the bottom surface 108 of the platform 104 is coupled to the upper portion of the second linkage system. The prosthetic foot device 100 may also include a base 110 coupled to the lower portion of the second linkage system.

In one example, the second linkage system has a shorter length and a shorter height than a length and a height of the first linkage system. Further, a maximum angle between the upper portion of the first linkage system and the lower portion of the first linkage system is between about ten and about twenty degrees, and a maximum angle between the upper portion of the second linkage system and the lower portion of the second linkage system is between about twenty and about forty-five degrees.

In yet another example, the linkage system 102 may comprise a first linkage system, and the prosthetic foot device 100 may further include a second linkage system and a third linkage system that each include all of the components of the linkage system 102 as described above. Such an arrangement may be similar to the embodiment shown in FIG. 10, with the linkage system 102 replacing the first linkage system 12, the second linkage system of the prosthetic foot device 100 replacing the second linkage system 14, and the third linkage system of the prosthetic foot device 100 replacing the third linkage system 15. In such an example, linkage system 102 may be an ankle linkage component of the prosthetic foot device 100, and the second linkage system may be a forefoot linkage component. The plane of rotation of the first linkage system 102 may be substantially parallel to the plane of rotation of the second linkage system. In other words, like components of the first linkage system 102 and the second linkage system are facing the same direction.

The plane of rotation of the third linkage system may be substantially perpendicular to the plane of rotation of the first linkage system and the plane of rotation of the second linkage system. In particular, the plane of rotation of the upper portion of the third linkage system is perpendicular to the plane of rotation of the upper portion of the first and second linkage systems. In such a configuration, the first linkage system and the second linkage system may enable medial-lateral movement, such as pronation and supination of the foot. The third linkage system may enable dorsiflexion and plantarflexion of the foot. While three linkage systems are described herein, any number of linkage systems similar to linkage system 102 may be added to the prosthetic foot device 10 to improve stability of the wearer.

The prosthetic foot device 100 may also include a platform 104 having a top surface 106 and a bottom surface 108, as discussed above. The bottom surface 108 of the platform 104 is coupled to the upper portion of the first linkage system, the bottom surface 108 of the platform 104 is coupled to the upper portion of the second linkage system, the top surface 106 of the platform 104 is coupled to the lower portion of the third linkage system. As discussed above, the plane of rotation of the upper portion of the third linkage system is perpendicular to the plane of rotation of the upper portion of the first and second linkage systems. The arrangements described above are merely embodiments of uses for the linkage system 102. As such, the linkage system 102 may be used in various prosthetic foot designs, as well as other prosthetic device designs.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A prosthetic foot device comprising:
   a linkage system comprising:
      an upper portion including a first contact surface;
      a lower portion having a second contact surface that contacts the first contact surface;
      a first pin having a first end and a second end, wherein the first pin is positioned through a first through-hole in the lower portion and further through a second through-hole in the upper portion; and
      a second pin having a first end and a second end, wherein the second pin is positioned through a third through-hole in the lower portion and further through a fourth through-hole in the upper portion, wherein the lower portion is rotatably coupled to the upper portion via the first pin and the second pin such that the lower portion rotates from a first position in which a top surface of the lower portion and a bottom surface of the lower portion are parallel to one another to a second position in which a non-zero angle exists between the top surface of the upper portion and the bottom surface of the lower portion, wherein the first through-hole in the lower portion comprises a first curved slot having a first width greater than a first diameter of the first pin such that the first pin moves laterally within the first curved slot as the lower portion rotates with respect to the upper portion from the first position to the second position, wherein the third through-hole in the lower portion comprises a second curved slot having a second width greater than a second diameter of the second pin such that the second pin moves laterally within the second curved slot as the lower portion rotates with respect to the upper portion from the first position to the second position, and wherein the second through-hole and the fourth through-hole in the lower portion each comprise a cylindrical through-hole.

2. The prosthetic foot device of claim 1, wherein the first contact surface of the linkage system comprises a convex surface, and wherein the second contact surface of the linkage system comprises a concave surface.

3. The prosthetic foot device of claim 2, wherein a contact between the first contact surface and the second contact surface of the linkage system comprises an instantaneous center of rotation of the upper portion with respect to the lower portion.

4. The prosthetic foot device of claim 1, wherein the first contact surface of the linkage system comprises a convex surface, and wherein the second contact surface of the linkage system comprises a convex surface.

5. The prosthetic foot device of claim 1, wherein the linkage system further includes at least one spring mechanism configured to return the linkage system to a position of repose when the linkage system is unweighted.

6. The prosthetic foot device of claim 1, wherein a length to height ratio of the linkage system is greater than 1.5:1.

7. The prosthetic foot device of claim 1, wherein the upper portion and the lower portion are solid, wherein the first through-hole in the lower portion extends from a first side of the lower portion to a second side of the lower portion, and wherein the second through-hole in the upper portion extends from a first side of the upper portion to a second side of the upper portion.

8. The prosthetic foot device of claim 1, wherein the lower portion is solid, wherein the second through-hole in the upper portion extends from a first side of the upper portion to a second side of the upper portion, wherein the upper portion further comprises a first sidewall spaced apart from a second sidewall, wherein the first sidewall includes the first contact surface and the second sidewall includes a third contact surface, wherein the second contact surface of the lower portion is configured to contact the first contact surface of the upper portion, wherein the third contact surface of the upper portion is configured to contact a fourth contact surface of the lower portion, wherein the first pin is positioned through the second through-hole in the upper portion, and wherein the first end of the first pin is positioned through the first through-hole in the first sidewall of the upper portion and the second end of the first pin is positioned through the third through-hole in the second sidewall of the upper portion such that the lower portion is rotatably coupled to the upper portion via the first pin.

9. The prosthetic foot device of claim 1, wherein the upper portion is solid, wherein the first through-hole in the lower portion extends from a first side of the lower portion to a second side of the lower portion, wherein the lower portion further comprises a third sidewall spaced apart from a fourth sidewall, wherein the first contact surface of the upper portion is configured to contact the second contact surface of the lower portion, wherein the first pin is positioned through the first through-hole in the upper portion, and wherein the first end of the first pin is positioned through the second through-hole in the third sidewall of the lower portion and the second end of the first pin is positioned through the fourth through-hole in the fourth sidewall of the lower portion such that the lower portion is rotatably coupled to the upper portion via the first pin.

10. The prosthetic foot device of claim 1, wherein the upper portion further comprises a first sidewall spaced apart from a second sidewall, wherein the first sidewall includes the first contact surface and the second sidewall includes a third contact surface, wherein the lower portion further comprises a third sidewall spaced apart from a fourth sidewall, wherein the third sidewall includes the second contact surface and the fourth sidewall includes a fourth contact surface, wherein the first contact surface of the upper portion is configured to contact the second contact surface of the lower portion and the third contact surface of the upper portion is configured to contact the fourth contact surface of the lower portion, wherein the first end of the first pin is positioned through the first through-hole in the first sidewall of the lower portion and further through the second through-hole in the third sidewall of the upper portion, and wherein the second end of the first pin is positioned through a third through-hole in the second sidewall of the lower portion and further through the fourth through-hole in the fourth sidewall of the upper portion such that the lower portion is rotatably coupled to the upper portion via the first pin.

11. The prosthetic foot device of claim 10, wherein each of the first through-hole and the third through-hole includes a bearing configured to receive the first pin.

12. The prosthetic foot device of claim 10, wherein the third sidewall of the lower portion includes a first cutout configured to receive a first protrusion of the first sidewall of the upper portion, and wherein the fourth sidewall of the lower portion includes a second cutout configured to receive a second protrusion of the second sidewall of the upper portion.

13. The prosthetic foot device of claim 10, wherein the third sidewall of the lower portion and the fourth sidewall of the lower portion are separate components, and wherein the first sidewall of the upper portion and the second sidewall of the upper portion are connected to thereby comprise a single component.

14. The prosthetic foot device of claim 1, wherein a first side of the lower portion moves further away from a first side of the upper portion as the lower portion rotates with respect to the upper portion in a first direction, and wherein a second side of the lower portion moves further away from a second side of the upper portion as the lower portion rotates with respect to the upper portion in a second direction.

15. The prosthetic foot device of claim 1, wherein the upper portion rotates with respect to the lower portion in a medial/lateral direction.

16. The prosthetic foot device of claim 1, further comprising:
a platform having a top surface and a bottom surface, wherein the top surface of the platform is coupled to the linkage system; and
a base coupled to the bottom surface of the platform.

17. The prosthetic foot device of claim 16, further comprising a housing positioned around at least a portion of the platform and the base.

18. The prosthetic foot device of claim 16, wherein the lower portion of the linkage system rotates with respect to the upper portion of the linkage system in a medial/lateral direction.

19. The prosthetic foot device of claim 16, wherein the platform and the base are coupled to one another via a toe cap.

20. The prosthetic foot device of claim 16, wherein the platform and the base each include a slot positioned therein and extending in a direction towards the linkage system to provide lateral flexibility of the prosthetic foot device when in use.

* * * * *